(12) United States Patent
Von Huben

(10) Patent No.: US 12,702,826 B2
(45) Date of Patent: Aug. 11, 2026

(54) ADVANCED IMPLANTED MAGNET MANAGEMENT IN THE FACE OF EXTERNAL MAGNETIC FIELDS

(71) Applicant: Cochlear Limited, Macquarie University (AU)

(72) Inventor: Mark Alan Von Huben, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 586 days.

(21) Appl. No.: 17/280,296

(22) PCT Filed: Dec. 26, 2019

(86) PCT No.: PCT/IB2019/061375
§ 371 (c)(1),
(2) Date: Mar. 26, 2021

(87) PCT Pub. No.: WO2020/136601
PCT Pub. Date: Jul. 2, 2020

(65) Prior Publication Data

US 2022/0032048 A1 Feb. 3, 2022

Related U.S. Application Data

(60) Provisional application No. 62/785,345, filed on Dec. 27, 2018.

(51) Int. Cl.
*A61N 1/08* (2006.01)
*A61N 1/36* (2006.01)

(52) U.S. Cl.
CPC .......... *A61N 1/08* (2013.01); *A61N 1/36038* (2017.08)

(58) Field of Classification Search
None
See application file for complete search history.

(56) References Cited

U.S. PATENT DOCUMENTS 7,566,296 B2 * 7/2009 Zimmerling .......... H04L 12/189 607/57
11,097,095 B2 * 8/2021 Smith .................. H04R 25/554
2011/0264172 A1 * 10/2011 Zimmerling ....... A61N 1/36036 607/60
2012/0223705 A1 * 9/2012 Lowery .................. A61B 5/055 324/307
2015/0010640 A1 * 1/2015 Marban ............. A61K 49/1875 424/179.1

(Continued)

FOREIGN PATENT DOCUMENTS

WO 2017105510 A1 6/2017

OTHER PUBLICATIONS

International Search Report & Written Opinion for PCT/IB2019/061375, mailed Apr. 23, 2020.

*Primary Examiner* — Erica S Lee
(74) *Attorney, Agent, or Firm* — Pilloff Passino & Cosenza LLP; Martin J. Cosenza

(57) ABSTRACT

A method, including subjecting a subcutaneous medical device containing a first magnet to a magnetic field of an MRI machine, thereby imparting a torque onto the first magnet and resisting the imparted torque via an external device that includes a second magnet, wherein the second magnet is movable relative to another component of the external device.

30 Claims, 22 Drawing Sheets

(56) References Cited

U.S. PATENT DOCUMENTS

| | | | |
|---|---|---|---|
| 2015/0374989 | A1 | 12/2015 | Hazard et al. |
| 2017/0312503 | A1 * | 11/2017 | Leigh ........................ A61N 1/08 |
| 2018/0270591 | A1 | 9/2018 | Kennes |

* cited by examiner 100
171
160
180
T1
137

ADVANCED IMPLANTED MAGNET MANAGEMENT IN THE FACE OF EXTERNAL MAGNETIC FIELDS

CROSS-REFERENCE TO RELATED APPLICATIONS

This application claims priority to U.S. Provisional Application No. 62/785,345, entitled ADVANCED IMPLANTED MAGNET MANAGEMENT IN THE FACE OF EXTERNAL MAGNETIC FIELDS, filed on Dec. 27, 2018, naming Mark Alan VON HUBEN of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is a method, comprising subjecting a subcutaneous medical device containing a first magnet to a magnetic field of an MRI machine, thereby imparting a torque onto the first magnet and resisting the imparted torque via an external device that includes a second magnet, wherein the second magnet is movable relative to another component of the external device.

In accordance with another exemplary embodiment, there is a method, comprising placing an MRI compatibility apparatus, including a magnet, against a recipient such that the apparatus at least generally aligns with an implanted magnet in the recipient due to magnetic attraction between the two magnets, wherein the magnet of the apparatus generates a magnetic force that is at least about 2 times as strong as a magnetic force generated by the implanted magnet as measured at a surface of the skin of the recipient closest to the implanted magnet and subjecting the recipient and the compatibility apparatus to an MRI field with the two magnets being subjected to the field.

In another exemplary embodiment, there is an MRI compatibility assembly, including a first component configured to interface with skin of a recipient at a location overlying an implanted magnet of an implantable component and a magnet supported by the first component and movable relative to the first component, wherein the MRI compatibility assembly is configured to be exposed to at least a 1T magnetic field of an MRI machine for at least 15 minutes.

BRIEF DESCRIPTION OF THE DRAWINGS

Embodiments are described below with reference to the attached drawings, in which:

FIGS. 10, 11, 12, and 13 present additional exemplary embodiments;

FIG. 16 presents another exemplary embodiment;

FIG. 17 presents details of an exemplary embodiment;

DETAILED DESCRIPTION

Exemplary embodiments will be described in terms of a cochlear implant. That said, it is noted that the teachings detailed herein and/or variations thereof can be utilized with other types of hearing prostheses, such as by way of example, bone conduction devices, DACI/DACS/middle ear implants, etc. Still further, it is noted that the teachings detailed herein and/or variations thereof can be utilized with other types of prostheses, such as pacemakers, muscle stimulators, etc. In some instances, the teachings detailed herein and/or variations thereof are applicable to any type of implanted component (herein referred to as a medical device) having a magnet that is implantable in a recipient.

Figure 1A:
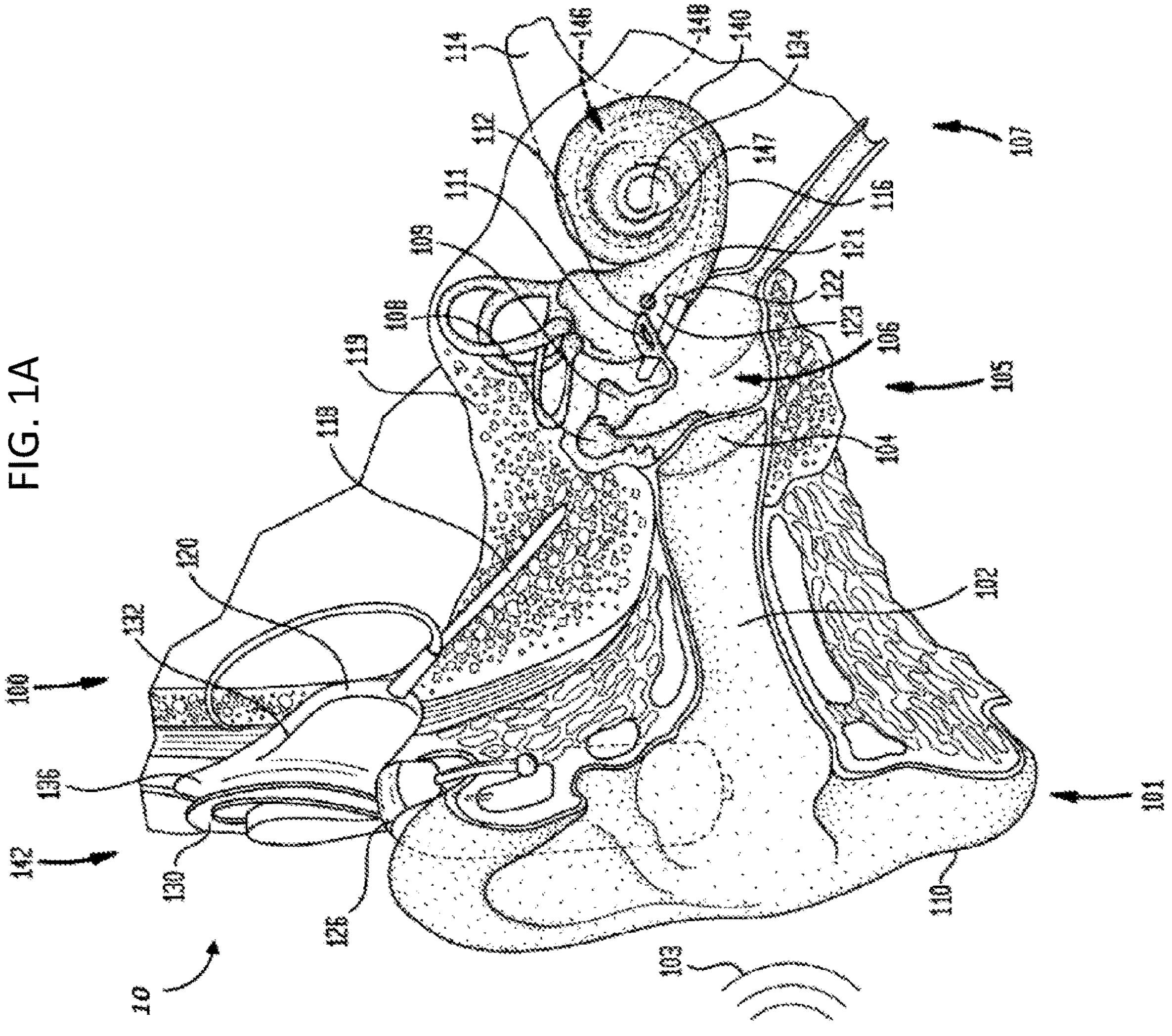
FIG. 1A is a perspective view of an exemplary hearing prosthesis in which at least some of the teachings detailed herein are applicable.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to other types of hearing prosthesis, such as by way of example only and not by way of limitation, bone conduction devices, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof that can have utility can be used in some embodiments of the teachings detailed herein.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant, and where the implanted cochlear implant includes a battery, that is recharged by the power provided from the external device 142.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1A is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil assembly 136. Internal coil assembly 136 typically includes a wire antenna coil comprised of multiple turns of electrically insulated single-strand or multi-strand platinum or gold wire, as will be described in greater detail below.

Cochlear implant 100 further comprises a main implantable component 120 and an elongate electrode assembly 118. Collectively, the coil assembly 136, the main implantable component 120, and the electrode assembly 118 correspond to the implantable component of the system 10.

In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone or via internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown in FIG. 1A) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123, or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 1B:
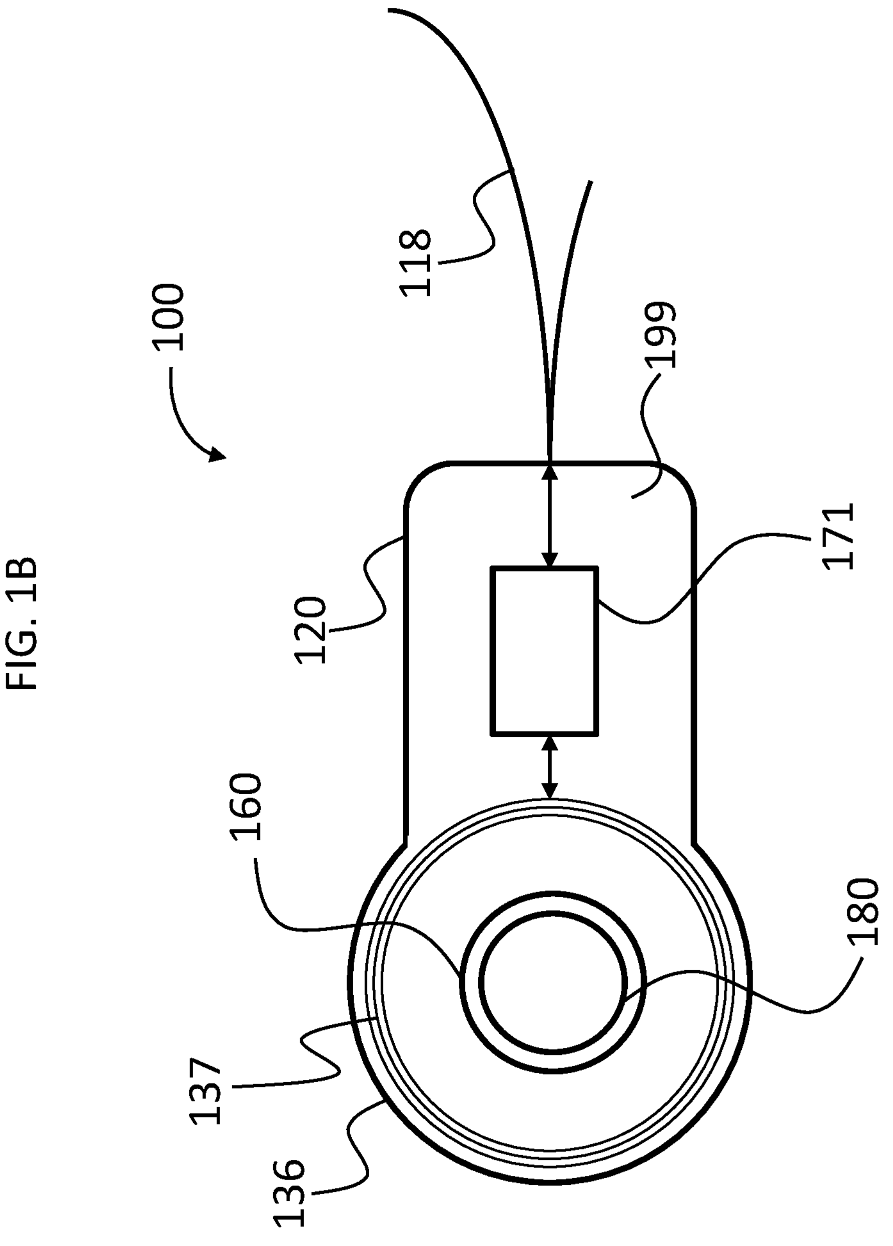
FIG. 1B is a top view of an exemplary hearing prosthesis in which at least some of the teachings detailed herein are applicable.

FIG. 1B depicts an exemplary high-level diagram of the implantable component 100 of the system 10, looking downward from outside the skull towards the skull. As can be seen, implantable component 100 includes a magnet 160 that is surrounded by a coil 137 that is in two-way communication (although in other embodiments, the communication is one-way) with a stimulator unit 171, which in turn is in communication with the electrode assembly 118.

Still with reference to FIG. 1B, it is noted that the stimulator unit 122, and the magnet apparatus 160 are located in a housing made of an elastomeric material 199, such as by way of example only and not by way of limitation, silicone. Hereinafter, the elastomeric material 199 of the housing will be often referred to as silicone. However, it is noted that any reference to silicone herein also corresponds to a reference to any other type of component that will enable the teachings detailed herein and/or variations thereof, such as, by way of example and not by way of limitation only, bio-compatible rubber, etc.

As can be seen in FIG. 1B, the housing made of elastomeric material 199 includes a hole 180 extending to the magnet apparatus 160. In an exemplary embodiment, the hole 180 has utilitarian value in that it can enable insertion and/or removal of the magnet apparatus 160 from the housing made of elastomeric material 199.

It is noted that magnet apparatus 160 is presented in a conceptual manner. In this regard, it is noted that in at least some embodiments, the magnet apparatus 160 is an assembly that includes a magnet surrounded by a biocompatible coating. Still further, in an exemplary embodiment, magnet apparatus 160 is an assembly where the magnet is located within a container having interior dimensions generally corresponding to the exterior dimensions of the magnet. This container can be hermetically sealed, thus isolating the magnet in the container from body fluids of the recipient that penetrate the housing (the same principle of operation occurs with respect to the aforementioned coated magnet). In an exemplary embodiment, this container permits the magnet to revolve or otherwise move relative to the container. Additional details of the container will be described below. In this regard, it is noted that sometimes the term magnet is used as shorthand for the phrase magnet apparatus, and thus any disclosure herein with respect to a magnet also corresponds to a disclosure of a magnet apparatus according to the aforementioned embodiments and/or variations thereof and/or any other configuration that can have utilitarian value according to the teachings detailed herein.

Figure 2:
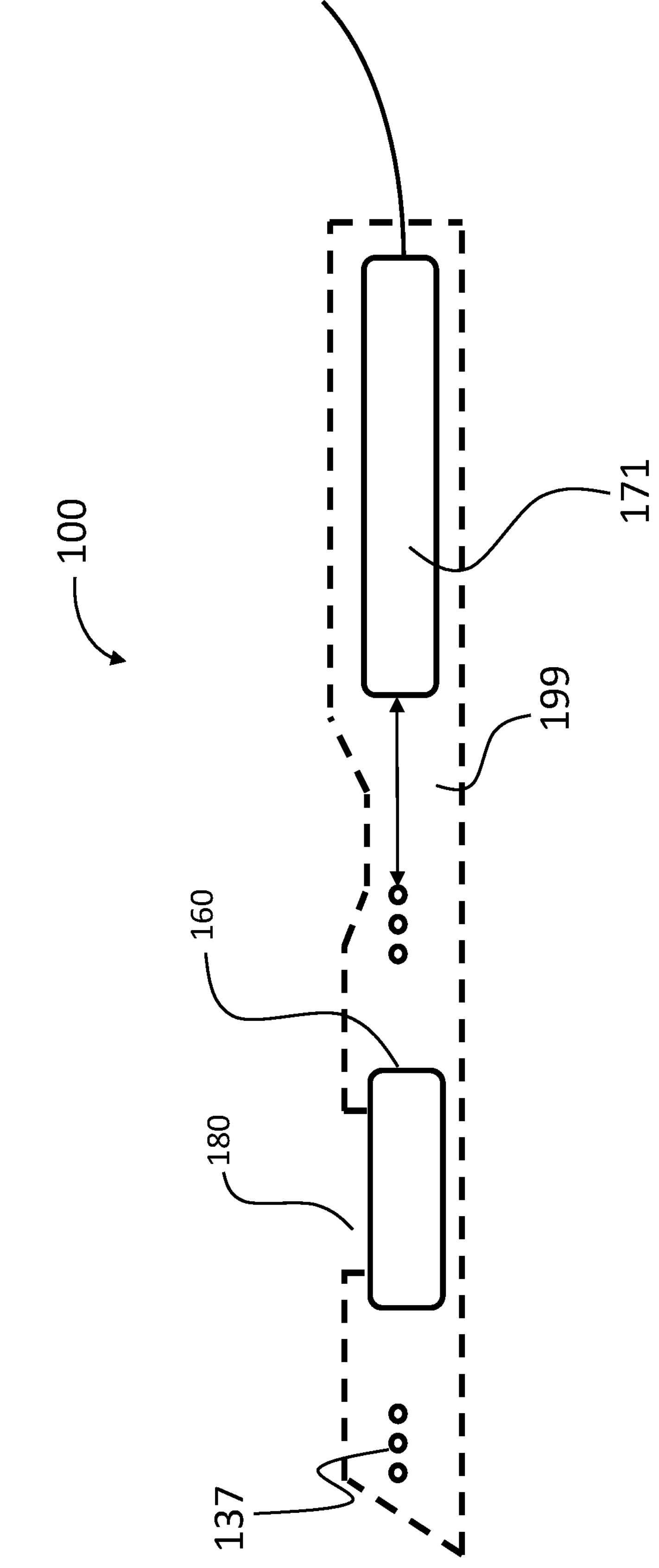
FIG. 2 is a side view of an exemplary hearing prosthesis in which at least some of the teachings detailed herein are applicable.

With reference now to FIG. 2, it is noted that the outlines of the housing made from elastomeric material 199 are presented in dashed line format for ease of discussion. In an exemplary embodiment, silicone or some other elastomeric material fills the interior within the dashed line, other than the other components of the implantable device (e.g., magnet, stimulator, etc.). That said, in an alternative embodiment, silicone or some other elastomeric material substantially fills the interior within the dashed lines other than the components of the implantable device (e.g., there can be pockets within the dashed line in which no components and no silicone is located).

It is noted that FIGS. 1B and 2 are conceptual FIGs. presented for purposes of discussion. Commercial embodiments corresponding to these FIGs. can be different from that depicted in the figures.

Figure 3:
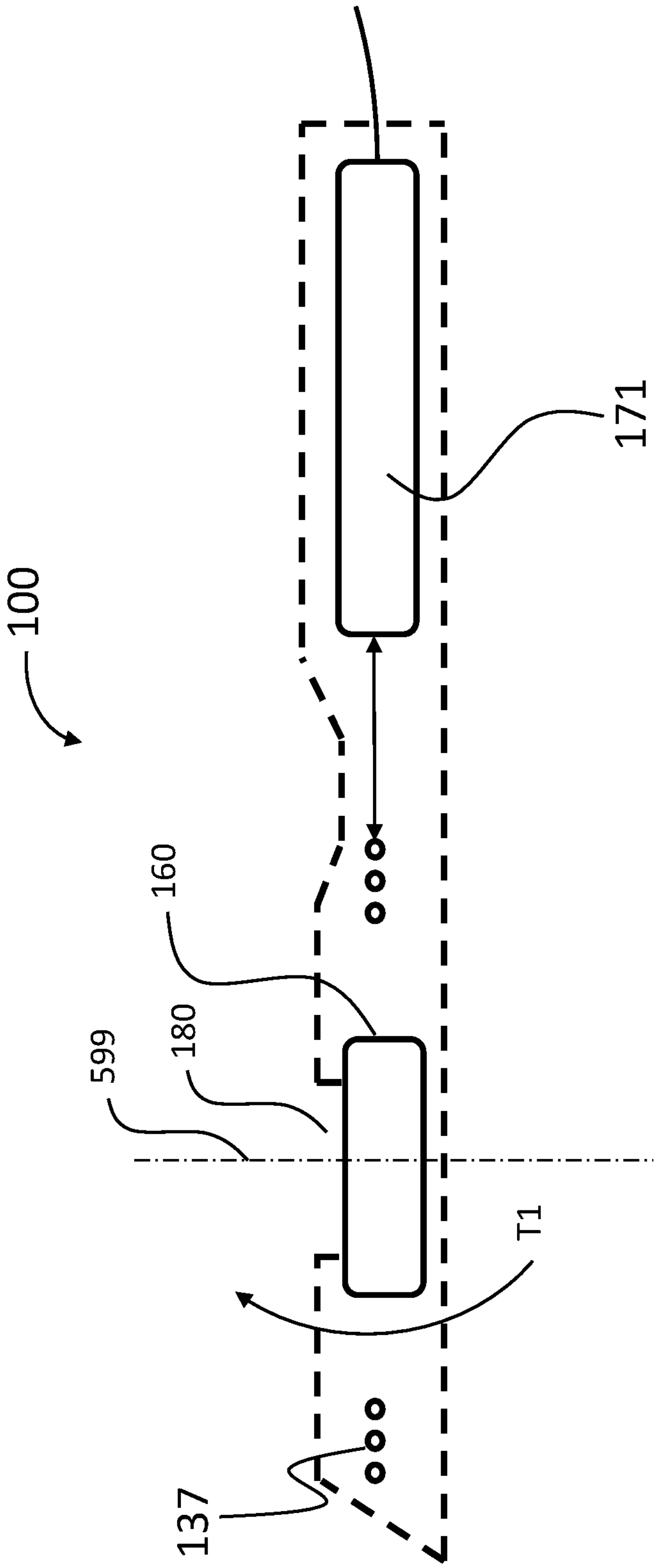
FIG. 3 is a reproduction of FIG. 2, except showing a functional representation of the application of a torque applied to the magnet 160.
Figure 4:
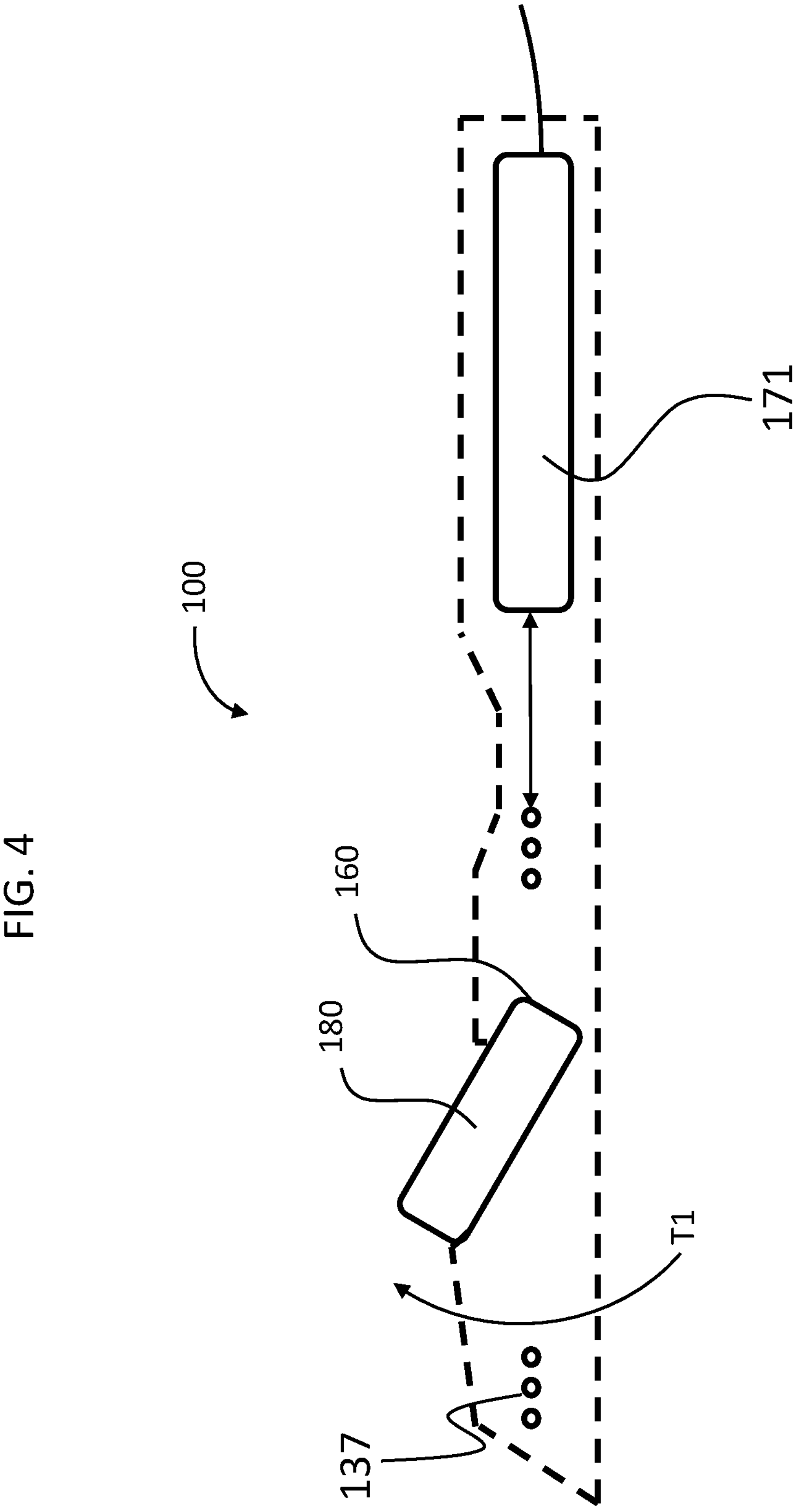
FIG. 4 depicts the exemplary hearing prosthesis of FIG. 2 where the torque applied to the magnet 160 has dislodged the magnet 160.

FIG. 3 depicts the implantable component 100 subjected to a magnetic field of an MRI machine. Specifically, FIG. 3 presents the magnet apparatus 160 of the implantable component 100 having a longitudinal axis 599. In this exemplary embodiment, the poles of the magnet of the magnet apparatus 160 are aligned with the axis 599. That is, in an embodiment where the magnet of the magnet apparatus 160 is a disk magnet (as is the case here), the poles are located on the flats. Thus, the magnet apparatus 160 has a north-south polar axis aligned with the longitudinal axis 599. As can be seen from FIG. 3, the magnetic field of the MRI machine imparts a torque, represented by arrow T1, on to the magnet apparatus 160. In a scenario where the magnetic field is strong enough, and the magnetic field is angled relative to the longitudinal axis 599 in a certain way, the torque T1 can be sufficiently strong enough so as to dislodge the magnet apparatus 160 from the pockets inside the housing 199 established by the silicon. This is functionally represented by FIG. 4, which depicts magnet 160 in a semi-dislodged state such that the silicone of the housing 199 has been deformed (permanently or non-permanently) relative to that which was the case prior to subjecting the magnet apparatus 162 the MRI magnetic field.

As noted above, the magnet apparatus of the implantable component 100 is a disk magnet apparatus/has the form of a short cylinder. That said, in an alternative embodiment, the magnets can have another configuration (e.g., a plate magnet, a bar magnet, etc.) or can be magnetically polarized in a different plane (e.g., a diametrically polarized magnet has a polar axis that is aligned with the diameter of a disc magnet, the width of a plate magnet, or the length of a bar magnet). Moreover, in an alternative embodiment, two or more magnets can be used in the implantable device and/or in the external device. The magnets could be located outboard of the coil. Any arrangement of magnet(s) of any configuration that can have utilitarian value according to the teachings detailed herein and/or variations thereof can be utilized in at least some implantable components. In any event, in at least some scenarios, a sufficiently strong magnetic field at the "correct" angle relative to the magnetic poles of the magnet of the magnet apparatus can result in dislodgment of the magnet apparatus (which encompasses complete removal of the magnet from the pocket in the implantable component 100, and the dislodgment depicted in FIG. 4H, etc.). There is utilitarian value with respect to applying a counterforce over the skin of the recipient to counteract the torque T1 that results from the magnetic field so as to avoid the dislodgment and/or discomfort to the recipient.

Figure 5:
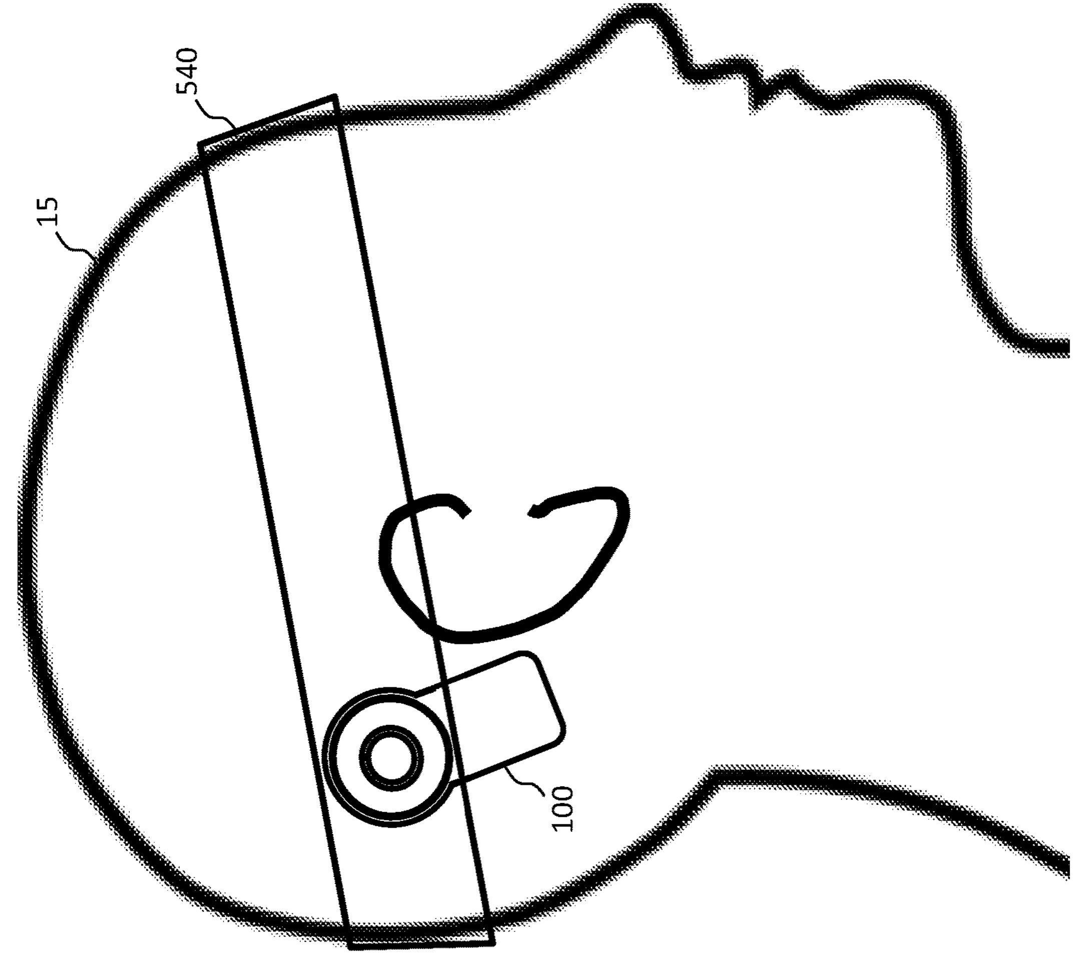
FIG. 5 depicts an exemplary belt utilized to apply force.

FIG. 5 depicts a side view of a human head 15 having implanted therein the implantable component 100. In an exemplary embodiment, a belt 540 extends about the head of the recipient. The belt 540 applies a compressive force over the skin of the recipient over the magnet apparatus 160 so as to counteract the torque T1 that results from the magnetic field. In an exemplary embodiment, the belt 540 can be bandage material wrapped around the head of the recipient in a manner concomitant with standard bandaging techniques. In some embodiments, the belt 540 can be nylon webbing or leather, and can have a buckle type apparatus to maintain tension on the material (or the material can be potentially tied off like one would do with the bandage material, or the material could be safety clipped (e.g., using a plastic safety pin), also like one could do with the bandage material. Any suitable biocompatible material that will not interfere with the magnetic field produced by the MRI machine can be utilized as the belt 540.

Figure 6:
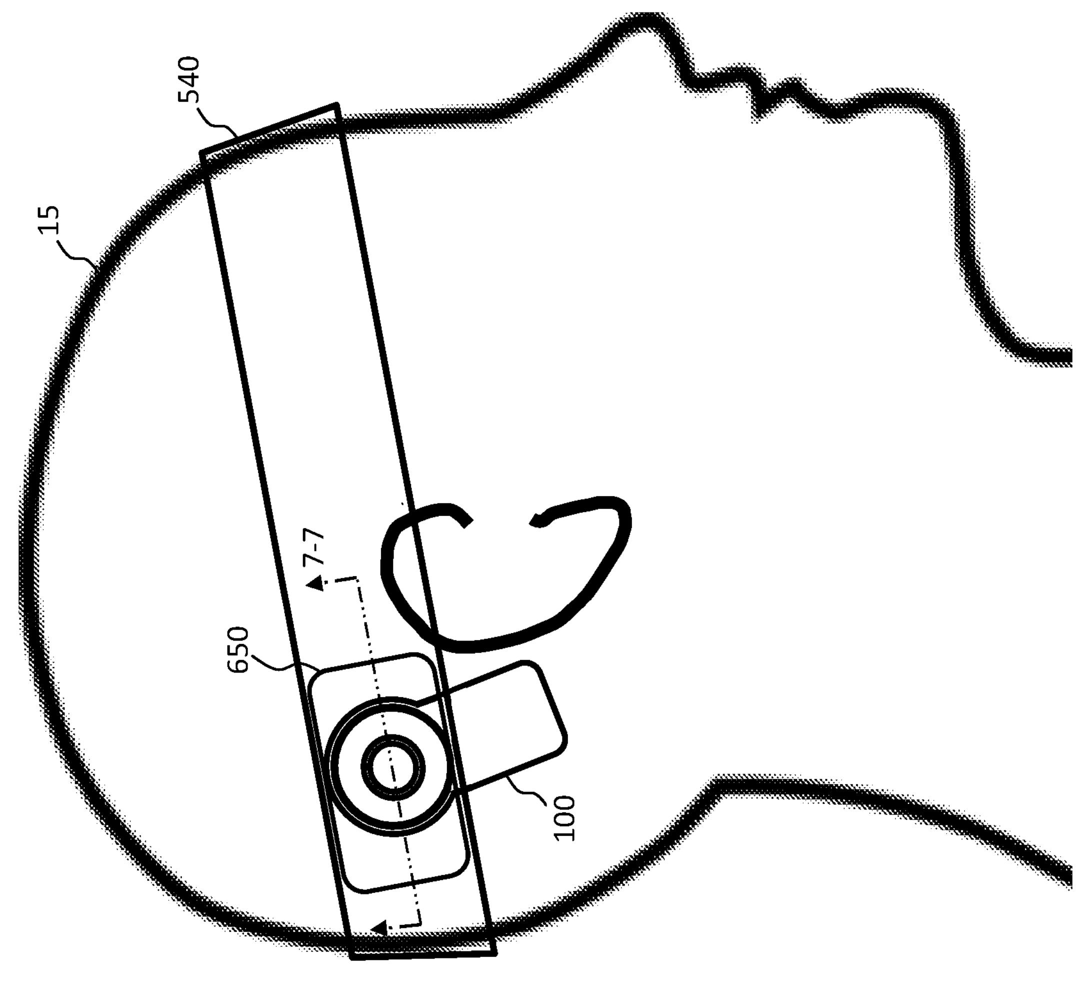
FIG. 6 depicts an exemplary MRI splint assembly utilizing the belts of FIG. 5.
Figure 7:
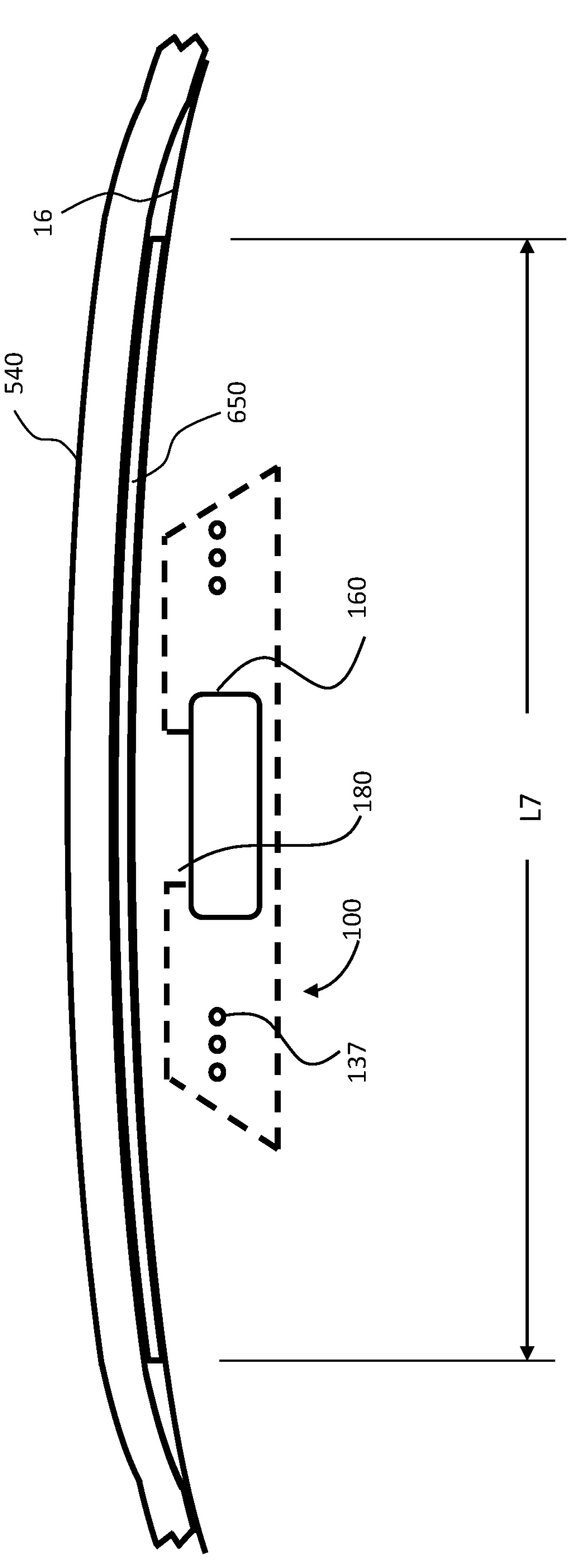
FIG. 7 depicts a cross-sectional view of a portion of the MRI splint assembly of FIG. 6.

FIGS. 6 and 7 depict an assembly that includes a belt 540 and a splint 650. In an exemplary embodiment, splint 650 is configured to contour to the outer skin of the recipient upon the application of sufficient attention to the belt 540 so that the splint 650 is pressed against the skin of the recipient, thus applying a force on the skin over the location of the magnet apparatus 160. FIG. 6 depicts the view of FIG. 5, and FIG. 7 depicts a cross-sectional view therethrough. As can be seen, the splint 650 is uniformly pressed against the outer surface 16 of the recipient 16 by the belt 540 (where, of course, hair could be located between the splint 650 and the skin of the recipient—in this regard, the scenario where hair is located between the splint and the skin of the recipient results in the splint being effectively in contact with the skin of the recipient). In an exemplary embodiment, the splint 650 provides a surface that is less deformable in the direction normal to the tangent surface of the skin over the magnet than that which is the case with respect to the material of the belt 540. For example, in the case of bandage material, the bandage material is still sufficiently flexible that a force applied to the material will cause the material to deform. In the case where a localized force is produced by movement of the magnet owing to the torque applied thereto by the magnetic field to the MRI, the material will deform by at least a certain amount, which may not be enough to provide a sufficient counterforce over the skin of the recipient to prevent the magnet from becoming dislodged. The splint 650 provides a less deformable surface, thus mitigating at least in part the localized deformation of the belt that would otherwise result. In an exemplary embodiment, the splint 650 is made of ABS plastic.

Figure 8:
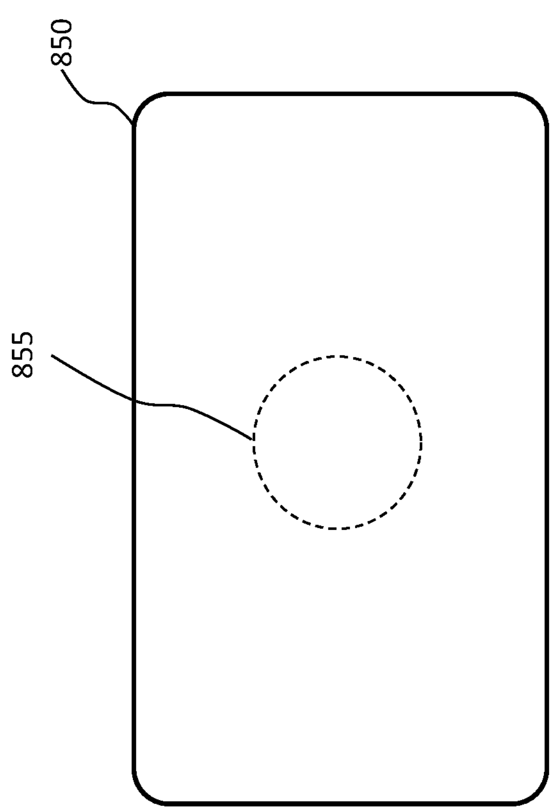
FIG. 8 depicts an enhanced MRI splint assembly according to an exemplary embodiment.

FIG. 8 provides another exemplary embodiment having utilitarian value according to the teachings detailed herein. Here, in this exemplary embodiment, a magnet 855 is embedded or otherwise located on the splint 850, which can correspond to any of the splints detailed herein and/or variations thereof. This magnet is a low strength magnet but one that has poles that are properly aligned with the magnet implanted in the recipient such that the fact is that the magnet 855 aligns the splint 850 with the implanted magnet, thus centering the splints 850 over the implanted magnet. In an exemplary embodiment, a healthcare professional applies the splint 850 against the side of the head of the recipient. If the poles of the magnet are aligned with those of the magnet implanted in the recipient, the splint 850 adheres to the head of the recipient. If not, the splint will repel, and thus the healthcare professional simply flips the splint over to the other side. Thus, in an exemplary embodiment, there is a device that automatically aligns with the magnet implanted in the recipient. In some alternate embodiments, instead of a magnet, a ferromagnetic material that is not magnet is utilized. This will provide at least partial alignment with the magnet implanted in the recipient. Via carefully adjusting the position of the splint 850, the healthcare professional can obtain a reasonably good centering of the splint 850 over the magnet. In this regard, the magnetic attraction will always be greatest when the center of the ferromagnetic material is directly over the center of the implanted magnet. Via a touch and feel method, the healthcare professional can obtain a rather accurate centering of the splint 850. Thus, in an exemplary embodiment, the MRI splint includes a means for generally automatically aligning the splints over a magnet implanted in the recipient, where the "general" caveat affords for the scenario where the component 855 is not a magnet is instead a ferromagnetic material.

In an exemplary embodiment, magnet 855 is a thin disk-shaped magnet, concomitant with the embodiment detailed above where the magnet 855 is embedded in the splint 850. In this regard, the magnet 855 is no thicker than the splint 850. Again, this is consistent with the fact that the magnet is a relatively low strength magnet, and thus there is relatively little magnetic material in the assembly. In some embodiments, the magnet 855 is entirely covered by the material of the splint 850, while in other embodiments, one or both sides of the magnet 855 extend or otherwise are accessible through openings on the respective sides of the splint 850.

In this regard, the embodiment of FIG. 8 results in a relatively low additional artifact in the results of the MRI scan because the magnet 855 is a weak magnet. Indeed, in the embodiment of FIG. 8, the magnet of the implantable component creates the artifact, and there is no additional artifact than that which results from the implanted magnet. In an exemplary embodiment, the magnet 855 generates a magnetic force that is less than the magnetic force that is generated by the implanted magnet, again, consistent with the fact that the magnet 855 is a relatively weak magnet. The magnet 855 is utilized for alignment purposes for the most part, and is typically so weak that the magnet cannot support the splint 850 against the recipient.

In an exemplary embodiment, the magnets detailed herein that are part of the compatibility device are configured to be effectively demagnetized when subjected to a MRI magnetic field when the magnet is used on the head of a recipient. In an exemplary embodiment, the magnet is configured to be effectively demagnetized upon exposure to an MRI magnetic field of at least 0.25, 0.5, 0.75, 1, 1.5, 2, 2.5, 3, 3.5, 4, 4.5, 5, 5.5T and/or 6T within less than 1, 2, 3, 4, 5, 6, 7, 8, 9, 10, 15, 20, 25, 30, 35, 40, 45, 50, 55, 60, 70, 80, 90, 100, 120, 130, 140, 150, 160, 170 or 180 or more seconds of exposure thereto.

In an exemplary embodiment, under the above circumstances, the magnet is configured to lose at least 50, 60, 70, 80, 90, 91, 92, 93, 94, 95, 96, 97, 98, 99 or 100% of its magnetism.

Figure 9:
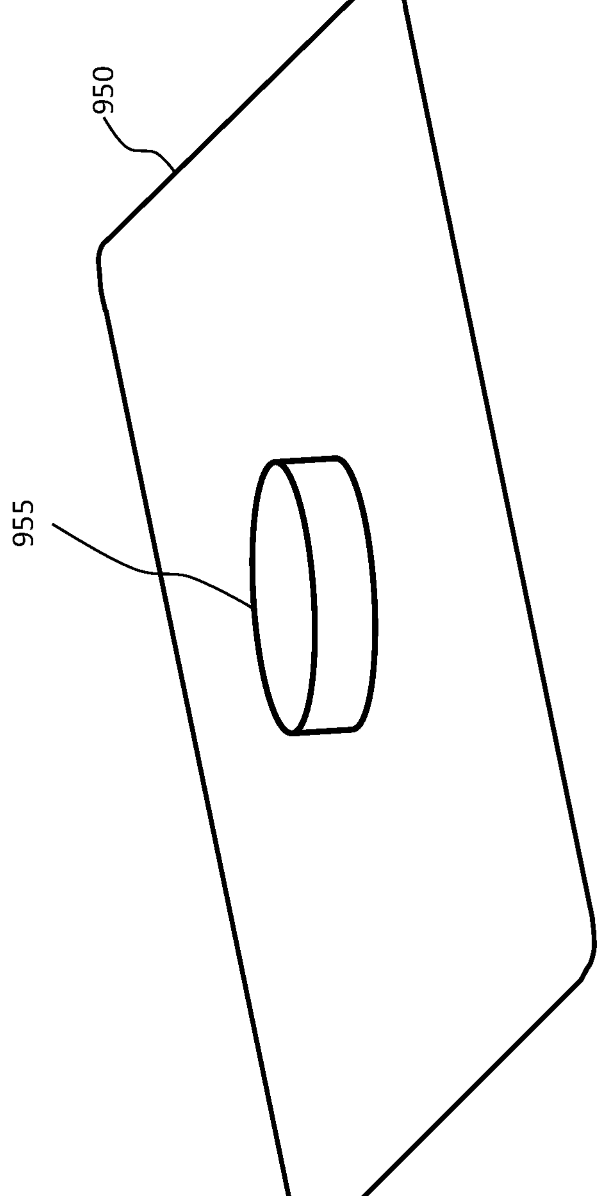
FIG. 9 depicts another exemplary embodiment of an MRI splint.

Conversely, the embodiment of FIG. 9 presents a different splint assembly from FIG. 8, where the magnet 955 is a stronger and larger magnet than that of the embodiment of FIG. 8. Here, magnet 955 is supported on splint 950. In an exemplary embodiment, magnet 955 is glued and/or bolted to the splint 950. In an exemplary embodiment, magnet 955 is many times stronger than the magnet 855 of the embodiment of FIG. 8.

Figure 10:
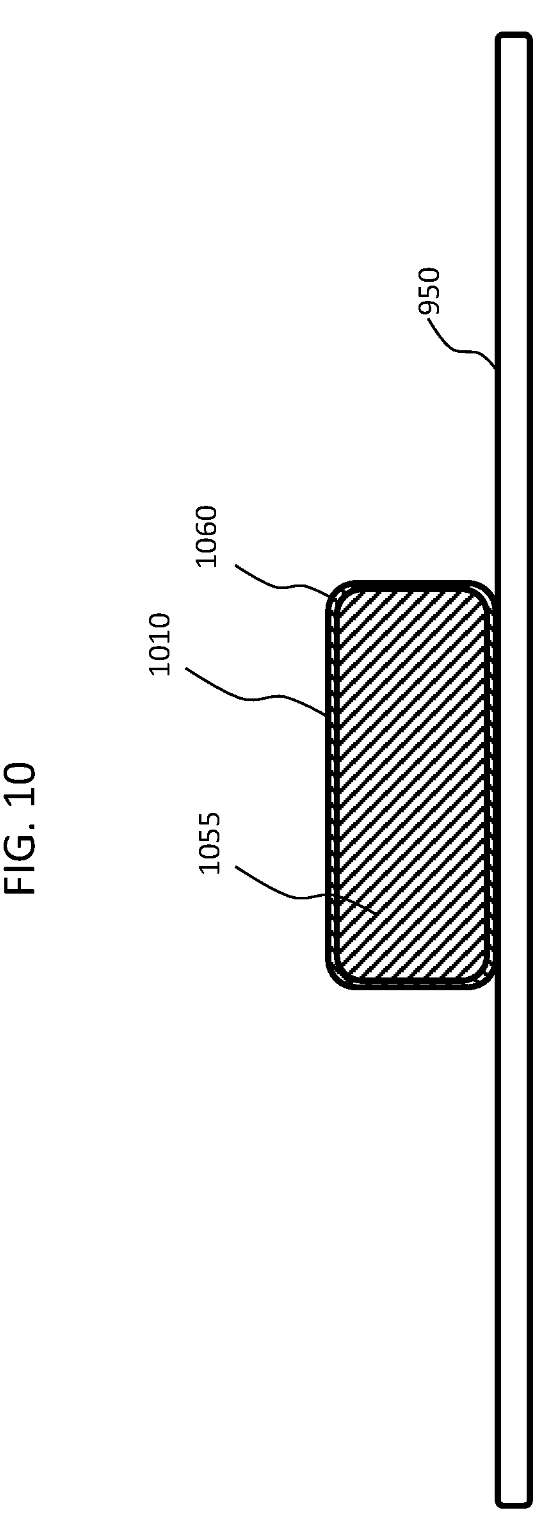

In at least some embodiments, a magnet apparatus is instead used instead of a plain magnet, where a magnet is encased in a case. That is, the magnet is covered by another structure. FIG. 10 depicts such an embodiment, where magnet 1055 is encased by housing 1060, the assembly establishing a magnet apparatus 1010. The housing 1060 is adhered to the splint 950 by any method that can enable such, such as glue, welding, etc.

In an exemplary embodiment, the magnet 1055 has a magnetic field that is axially aligned. In an exemplary embodiment of use, the splint is placed over the skin that overlies the implanted component of the prostheses, and the magnetic field of the magnet 1055 interacts with the magnetic field of the implanted magnet. In an exemplary embodiment, the implanted magnet is a disk magnet that has its magnetic field axially aligned. In an exemplary embodiment, where the north pole of the implanted magnet is closer to the skin surface than the south pole, the north pole of magnet 1055 will be located on the side away from the splint 950. Thus, the magnetic field will flow from the implanted magnet into the bottom surface of the external magnet 1055, out of the top surface of the external magnet 1055 and then around the sides of the external magnet and around the sides of the implanted magnet and into the bottom surface of the implanted magnet, and so on. In an exemplary embodiment, this magnetic field aligns the external magnet with the implanted magnet, and thus aligns the splint 950 over the implanted magnet. In an exemplary embodiment where the magnet 1055 is centered on the top surface of the splint 950, the splint 950 will be centered over the implanted magnet as well. In an exemplary embodiment, a low friction surface of the splint 950 on the side away from the magnet 1055 is utilized so as to reduce any forces that would resist centering of the magnets, and thus centering of the splint 950.

Thus, in an exemplary embodiment, there is an MRI compatibility assembly that is configured such that the magnet supported by a component thereof at least generally automatically aligns the assembly in general, and a component supporting the magnet in particular, with the implanted magnet.

Figure 11:
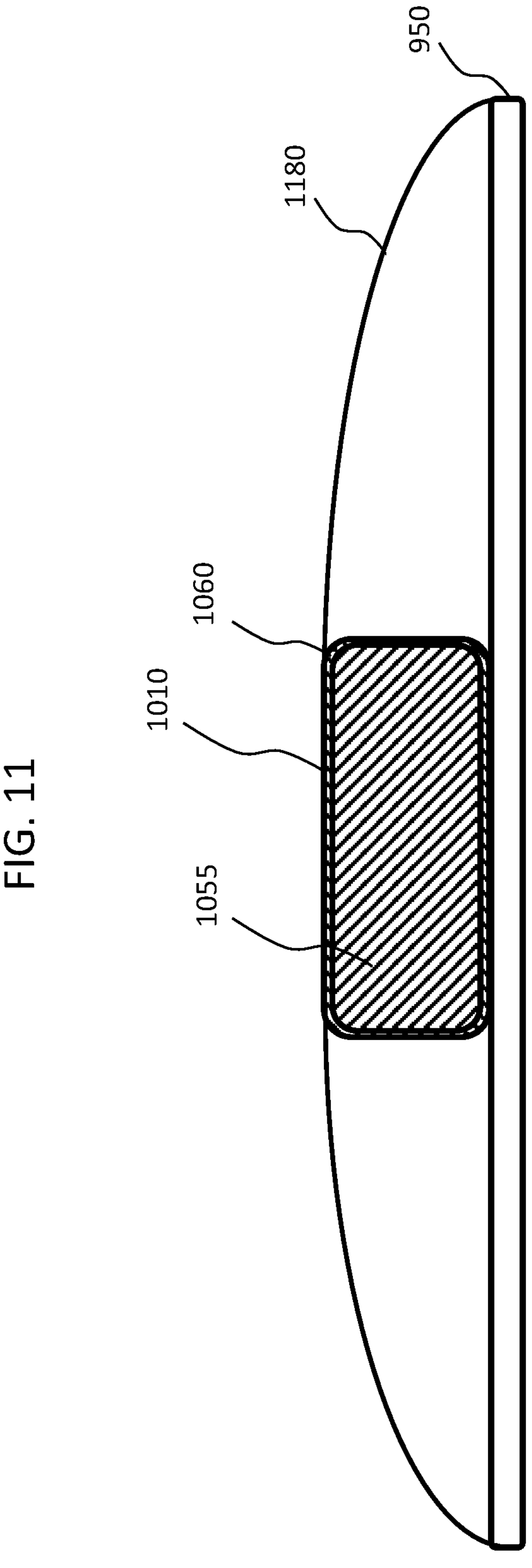

At least some exemplary embodiments will utilize the belt 540 or the like (as noted above, bandages can be used, etc.). There can be utilitarian value with respect to providing a contoured device. FIG. 11 depicts an exemplary splint 1150 that can correspond to the splint of FIG. 10, except that the larger magnet 1055 is embedded in a curved body 1180 that is located on top of the splint 950, as can be seen. The belts or bandages can be placed over the curved body 1180 to apply compression in accordance with the teachings detailed herein. In an exemplary embodiment, the body 1180 can apply a downward force, such as, for example, a spring force (in some embodiments, the force is not a spring force) onto the splint 950 so as to contour the skin facing side of the splint (bottom) to the skin of the recipient/curvature of the head of the recipient. In an exemplary embodiment, the belt/bandage is a body that does not stretch, and/or applies a small downward force and/or resists upwards forces. This can be achieved via a belt/bandage that does not stretch. In some embodiments, stretching is minimal. In some embodiments, this is not the case.

In an exemplary embodiment, the belt/bandage is configured to stretch no more than 10, 9, 8, 7, 6, 5, 4, 3.5, 3, 2.5, 2, 1.5, 1.25, 1, 0.75, 0.5, 0.25, 0.2, 0.15, 0.1, 0.05, 0.04, 0.03, 0.02, 0.01, 0.005, 0.004, 0.003, 0.002 or 0.001 percent relative to the overall circumference or any value or range of values therebetween in 0.001 percent increments.

Figure 12:
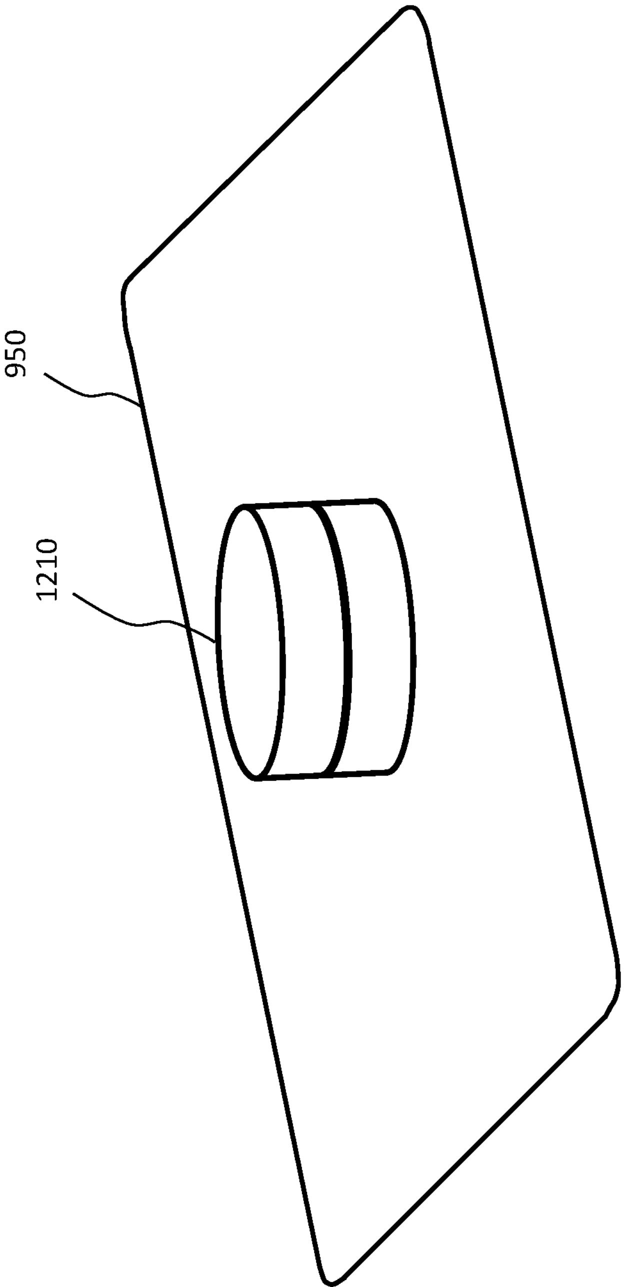

FIG. 12 presents an alternate embodiment of a splint 950 with a magnet apparatus 1210. Here, the magnet apparatus 1210 includes a split casing, as can be better seen in FIG. 13. Here, a top housing portion 1364 is shown in an exploded view and separate from the bottom housing portion 1362. The housing portions are hollow and have respective cylindrical basins 1399, which, when the housing portions are connected to one another, house the magnet 1355. In an exemplary embodiment, the magnet 1355 is glued into the basin(s) of the housing(s), while in other embodiments, the magnet 1355 is configured to spin within the basin. There can be utilitarian value with respect to allowing the magnet 1355 to spin, such as when exposed to a magnetic field of the MRI machine, the magnet can attempt to align itself with that MRI field. In this exemplary embodiment, the magnetic field could be aligned diametrically as opposed to axially.

Figure 13:
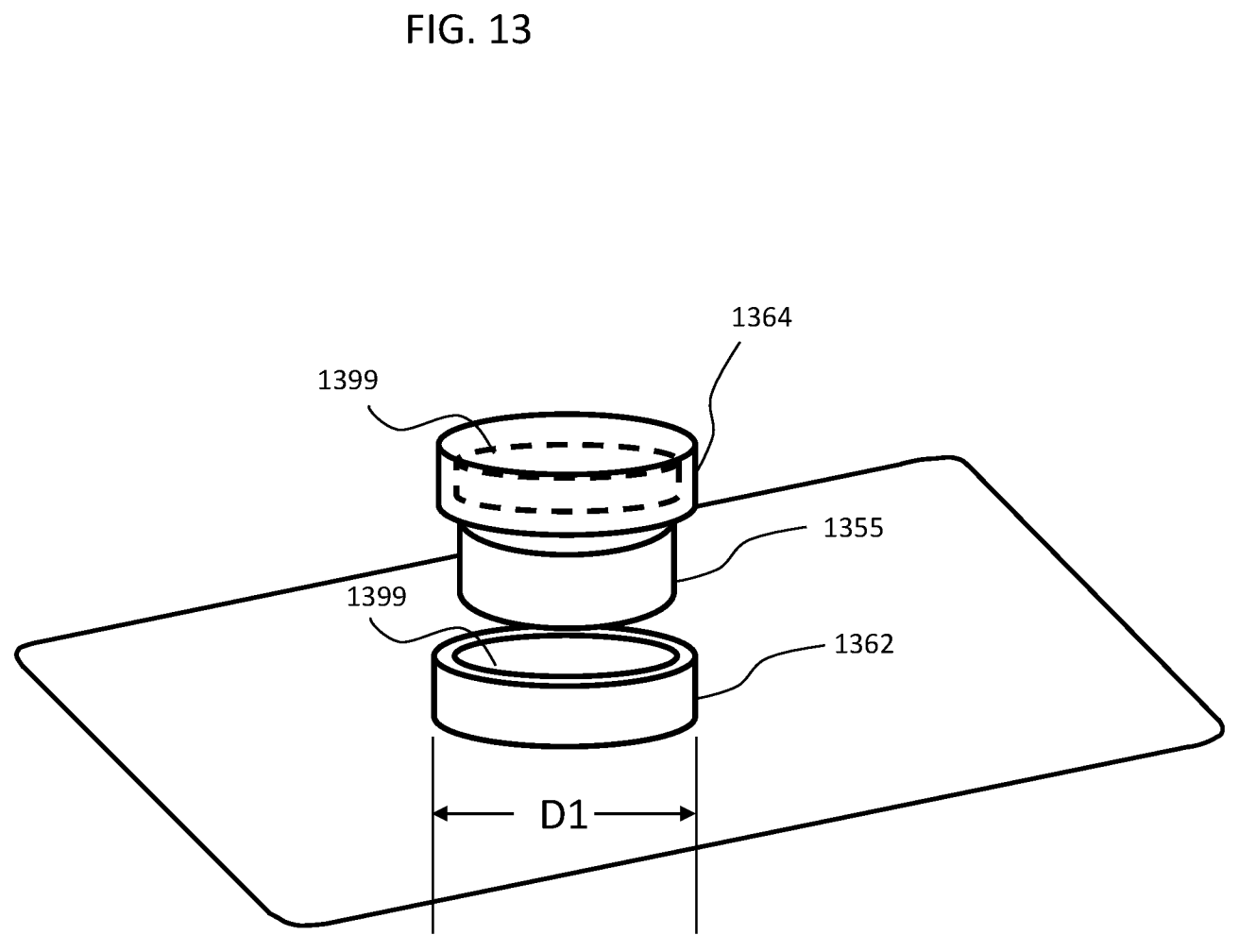

FIG. 13 presents dimension D1, where dimension D1 is the largest diameter of the housing portion 1362 (and thus housing portion 1364 where the two components are identical but mere each other), where D1 is 10, 11, 12, 13, 14, 15, 16, 17, 18, 19, 20, 21, 22, 23, 24, 25, 26, 27, 28, 29, or 30 mm or any value or range of values therebetween in 0.1 mm increments.

In an exemplary embodiment, the splint 950 corresponds to a splint that meets the requirements of ISO/IEC 7810 as of Apr. 17, 2016, for an identification card that is an ID-1 identification card per that specification. In an exemplary embodiment, the splint 950 corresponds to a splint having a length that is 85.60 mm, a width corresponding to 53.98 mm, and a thickness of 0.76 mm. In an exemplary embodiment, the splint 950 can be a splint that meets all of the requirements of the ISO standard but for the thickness (and thus the rigidity), where the thickness is about 1.0 mm, 1.01 mm, 1.02 mm, 1.03 mm, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.4, 1.45, 1.5, 1.55, 1.6, 1.65, 1.7, 1.75, 1.8, 1.85, 1.9, 1.95, or 2 mm, or more, or any value or range of values therebetween in about 0.005 mm increments. In an exemplary embodiment, the length of the splint is 50, 55, 60, 65, 70, 75, 80, 85, 90, 95, 100, 105, 110, 115, 120 mm or any value or range of values therebetween in 0.1 mm increments, and the width of the splint is 20, 25, 30, 35, 40, 45, 50, 55, 60, 65, 70, 75, 80, or 85 mm or any value or range of values therebetween in 0.1 mm increments.

Figure 14:
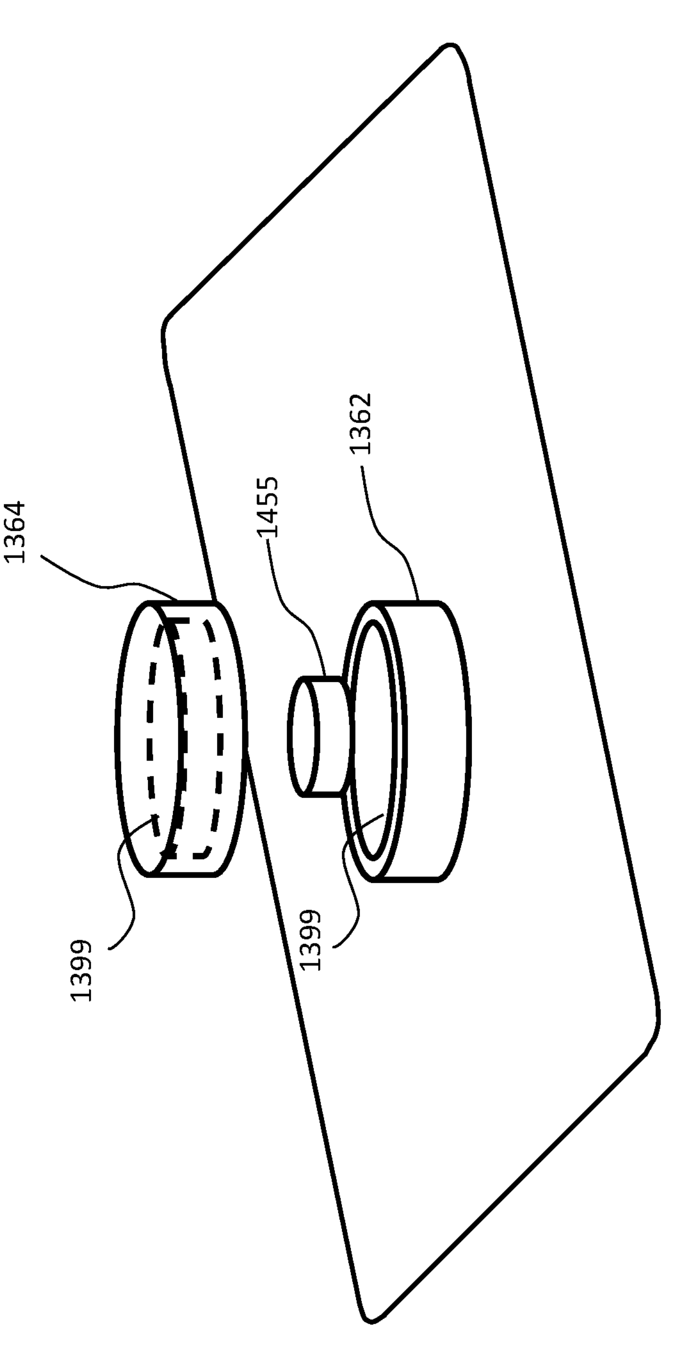
FIG. 14 presents another embodiment that enables the magnet to move relative to the housing and/or splint.

One drawback with the embodiment of FIG. 13, indeed, with the embodiments of FIGS. 9 and 10 as well, is that if the implanted magnet as a North-South polarity that is different than the polarity of the external device with respect to the polarity relative to the splint, the splint may not be able to be placed onto the recipient with the splint in contact with the skin over the magnet. The splint would instead want to flip over to have a N-S-N-S alignment with respect to the two magnets. FIG. 14 presents an alternate embodiment they can have utilitarian value with respect to ensuring that the splint side can always be placed against the skin. Here, the magnet 1455 is smaller than the magnet 1355, and the basins permit the magnet 1455 to flip within the housing portions when the housing portions are connected to each other. Thus, in an exemplary embodiment, if the N-S alignment of the magnet of the external component is opposite of that of the implanted magnet, when the healthcare professional places the splint over the implanted magnet, the magnet 1455 will flip to align the poles if the pole are not already aligned. This can ensure that the splint side is always closest to the implanted magnet.

Figure 15:
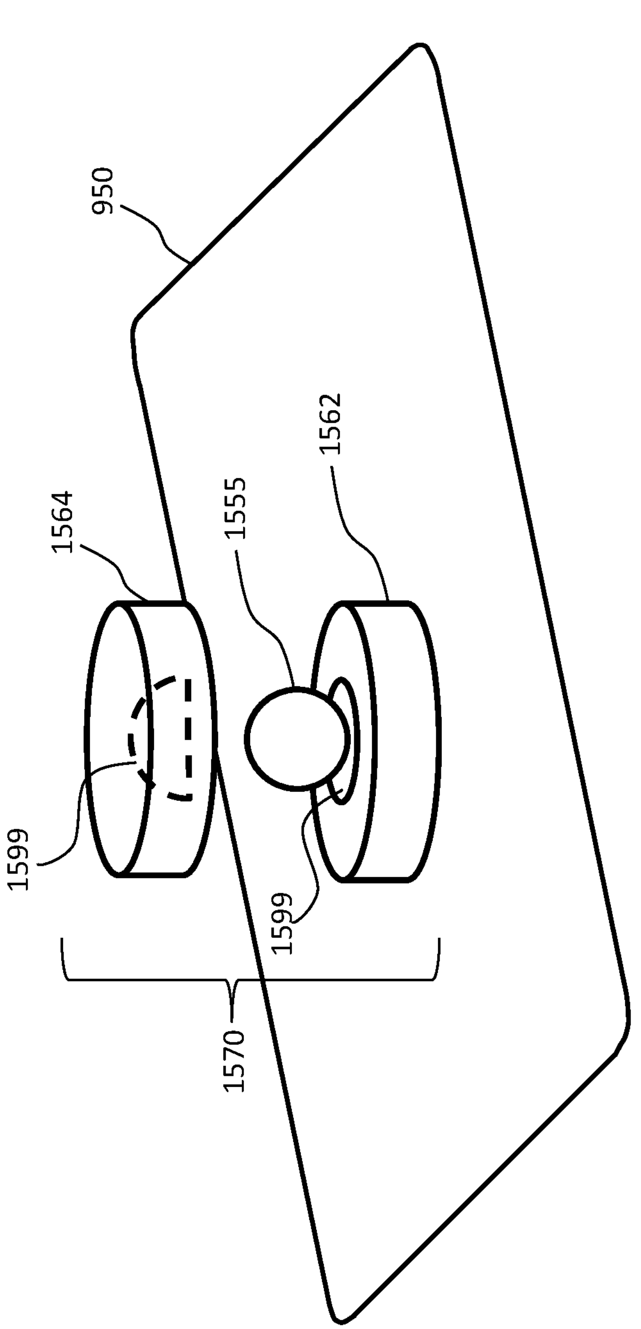
FIG. 15 presents another exemplary embodiment.

FIG. 15 presents yet another alternate embodiment of a splint 950 with a top housing portion 1564 and a bottom housing portion 1562, both of which include a basin 599, where the basin 1599 is a hemispherical shape. In this embodiment, the magnet 1555 is a spherical magnet and is retained in the basins when the top housing portion is connected to the bottom housing portion. In an exemplary embodiment, spherical magnet 1555 is enabled to rotate/revolve within the housing that is established by the housing portions 5462 and 1564. In an exemplary embodiment, the spherical magnet is permitted to rotate only about one axis while in other embodiments the spherical magnet is permitted rotate about any axis. In an exemplary embodiment, this can permit the magnetic field of the magnet 1555 to align itself with the magnet that is implanted in the recipient and/or with the magnetic field of the MRI device. Here, it is not necessary for there to be room for the magnet to flip, more accurately, by contouring the basins to the contour of the spherical magnet 1555, the spherical magnet 1555 can rotate in any direction. In an exemplary embodiment, low friction/antifriction features are located within the housing. For example, ball bearings can be placed in between the walls of the basins and the magnet 1555. In an exemplary embodiment, a lubricating oil can be located in the basins. Any arrangement that can enable the spherical magnet 1555 to rotate within the cavity established by the basins can be utilized in at least some exemplary embodiments.

It is noted that some embodiments include utilizing the curved body of the embodiment of FIG. 10 with the moving magnet embodiments. That said, in an alternate embodiment, there can be utilitarian value with respect to utilizing the face of the housing as the compression face that faces/contacts the head of the recipient. In this regard, there can be utilitarian value with respect to utilizing the device of FIG. 15 or FIG. 14 or FIG. 13, etc., where the splint 950 is located away from the head/the housing is located between the head in the splint 950. In an exemplary embodiment, the belt 540 or bandages, etc., are wrapped around and/or placed over the splint 950 so that the splint spreads out the area of contact with the bandages over a greater area than that which would otherwise be the case with respect to utilizing the housing alone.

Thus, there can an MRI compatibility assembly where a maximum diameter of the assembly at a location away from a skin interfacing portion is larger than a maximum diameter of the assembly at a location proximate the skin interfacing portion.

Figure 16:
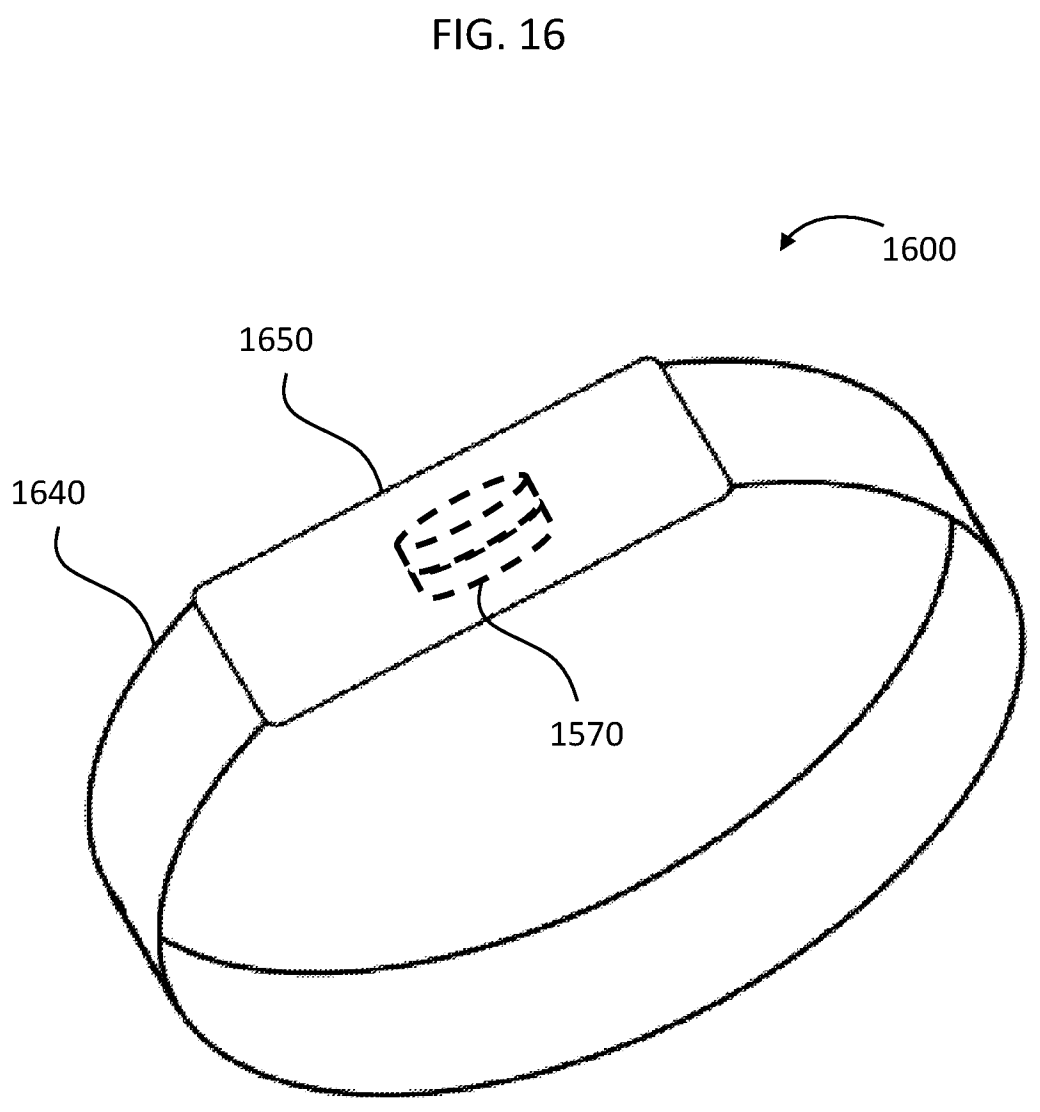

In an exemplary embodiment, the magnet apparatus (magnet apparatus 1570, to pick one embodiment for example), can be secured to an apparatus that holds the magnet/magnet apparatus in place. In an exemplary embodiment, there is a method that includes securing the external device to the head of the recipient by extending a belt about the head and tensioning the belt. As noted above, the belt can be a general bandage or can be a specific apparatus specially designed for this method. By way of example only and not by way of limitation, the splints can have holes/slots located at the opposite ends in the length direction through which a nylon webbing extends, and the nylon webbing can have a belt buckle like device or a Velcro device to enable the tensioning, or more accurately, the maintenance of the tension on the belt. In this regard, FIG. 16 depicts an exemplary embodiment of an MRI splint that includes an adjustable Velcro belt 1640 and a splint 19650 which can correspond to any of the splints detailed herein and/or variations thereof. In the embodiment depicted in FIG. 16, the belt 1640 is attached to the very ends of the splint 1650. In an alternate embodiment, the belt 16940 extends about the top surface of the splint 1650 so as to encircle the splint 1650, albeit with the splint 1650 located on the inside diameter of the belt 1640. As see in dashed lines, magnet apparatus 1570 is located on the inside of the belt loop/located on the splint 6501 the side faces the recipient. The belt 1640 can be used to hold the splint, and thus the magnet apparatus 1570, in position over the implant magnet while a supplementary bandage or similar restraint is used to apply sufficient compressive force for the MRI procedure. Alternately, the belt 1640 illustrated in FIG. 16 can be used in at least some embodiments to apply sufficient compressive force without supplementary bandaging. Some additional details of the utilization of Velcro or other types of belts can be utilized in at least some exemplary embodiments.

Figure 17:
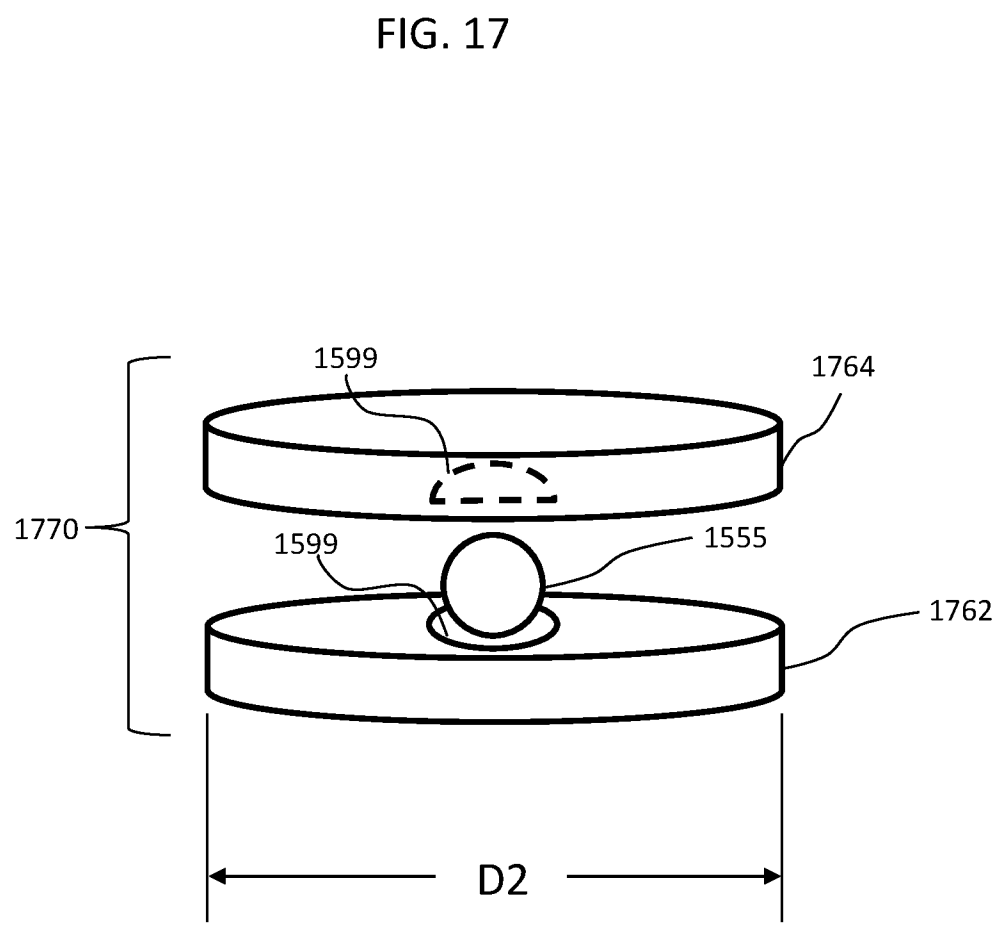

The above said, in some embodiments the belt and/or the splint can be dispensed with entirely, and the magnet apparatus and bandages can be used without these components. FIG. 17 presents an exemplary embodiment of a magnet apparatus 1770, which includes a housing portion 1764 in the form of a disk or cylinder with a hemispherical basin 1599 corresponding to the basin above, and a housing portion 1762 in the form of a disk or cylinder with a hemispherical basin 1599, again corresponding to the basin above. Here, spherical magnet 1555 is located in the cavity established by the basins. When the housing portions are connected to each other, the basins form a spherical cavity in which the spherical magnet 1555 can rotate in any direction in some embodiments, and can rotate in only one direction and other embodiments. The housing can be made of PEEK, or vinyl, or any polymer that can have utilitarian value/is compatible with a skin of a person, or can be made of titanium or other metals, etc.

In this exemplary embodiment, the surface area of the housing portion that faces the skin is larger than the corresponding surface area of the housing portions of the embodiments above. In this regard, the housing portion at least partially has the functionality of the splints detailed above. In an exemplary embodiment, D2 is less than, greater than or equal to 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 mm, or any value or range of values therebetween in 0.1 mm increments (e.g., 33.3 mm, 44.4 mm, 25.3 to 55.4 mm, etc.). Thus, in some embodiments, the assembly has a skin interfacing side surface that is between any two of the aforementioned values of D2 at its maximum diameter. In an exemplary embodiment, the housing portion provides a skin interfacing surface area of less than, greater than or equal to 500, 1000, 1500, 2000, 2500, 3000, 3500, 4000, 4500, 5000, 5500, 6000, 6500, 7000, 7500, or 8000 $mm^2$ or any value or range of values therebetween in 1 $mm^2$ increments. Thus, in some embodiments, there is an MRI compatibility apparatus that interfaces with no more than about 500, 1000, 1500, 2000, 2500, 3000, 3500, 4000, 4500, 5000, 5500, 6000, 6500, 7000, 7500, or 8000 $mm^2$ or any value or range of values therebetween in 1 $mm^2$ increments of recipient body surface when the two magnets are interacting with one another.

The maximum, minimum and/or average (mean or median or mode) height of the magnet apparatus 1770 can be less than, greater than or equal to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 mm or any value or range of values therebetween in 0.1 mm increments. In an exemplary embodiment, the maximum, minimum and/or average (mean or median or mode) height of the magnet apparatus 1770 can be less than, greater than or equal to 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3 or more times the value of D2 or any value or range of values therebetween in 0.01 increments. Thus, in an exemplary embodiment, a height of the MRI compatibility apparatus is at least about one third, a half, two thirds or three quarters of a maximum diameter of the MRI compatibility apparatus.

Also, in an exemplary embodiment, the maximum diameter of the magnet is less than, greater than and/or equal to greater than or equal to 10, 11, 12, 13, 14, 15, 16, 17, 18, 19, 20, 21, 22, 23, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 mm, or any value or range of values therebetween in 0.1 mm increments.

In view of the above, it can be seen that in an exemplary embodiment, there is an MRI compatibility assembly, comprising, a first component (the splint, the housing/portion of the housing encasing the magnet, etc.) configured to interface with skin of a recipient at a location overlying an implanted magnet of an implantable component. This assembly can further include a magnet supported by the first component. In an exemplary embodiment, the magnet is fixed to the first component, while in other embodiments, the magnet is movable relative to the first component. Here, the MRI compatibility assembly is configured to be exposed to at least a 1, 1.5, 2, 2.5, 3, 3.5, 4, 4.5, 5, 5.5 or 6T or any value or range of values therebetween in 0.1 T increments magnetic field of an MRI machine for at least 5, 10, 15, 20, 25, 30, 35, 40, 45, 50, 55, 60, 70, 80, or 90 or more minutes or any value or range of values therebetween in 1 minute increments. In an exemplary embodiment, the magnet supported by the first component is a disk magnet, and the disk magnet is rotatable about an axis thereof. In an exemplary embodiment, the magnet supported by the first component is a spherical magnet, and the spherical magnet rotates when it interacts with the magnetic field of the MRI machine about at least one axis, and in other embodiments, the spherical magnet can rotate in any direction. in some embodiments, the magnet supported by the first component magnet is a magnet that produces a magnetic field of at least about a third, or a half or two thirds or three quarters or one Tesla. In an exemplary embodiment, the magnet supported by the first component magnet is a magnet that produces a magnetic field of at least about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 T or any value or range of values therebetween in 0.01T increments.

Figure 18:
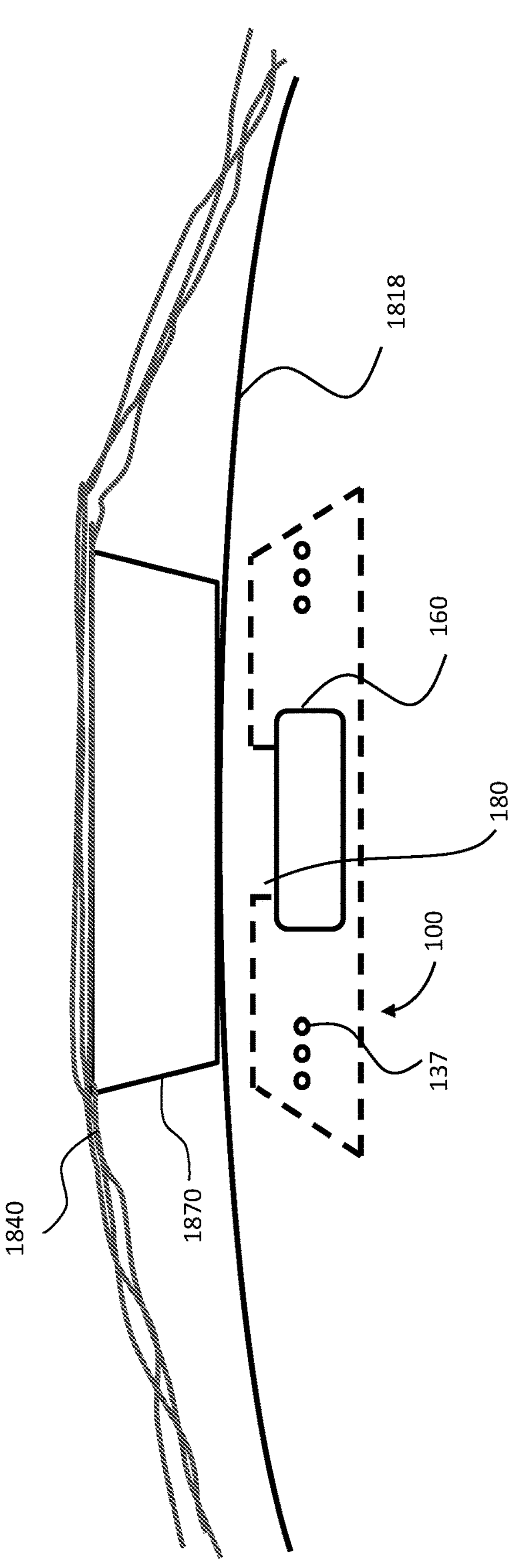
FIG. 18 presents another exemplary embodiment.

FIG. 18 presents a side view of an exemplary embodiment of a magnet apparatus 1870 that is held against skin 1818 of a recipient's head over an implantable medical device having a magnet using bandages 1840. The magnet apparatus 1870 can correspond to any of the magnet apparatuses detailed herein. However, this exemplary magnet apparatus can include any of the magnets detailed herein and can have any of the cavities detailed herein for the magnet. In this embodiment, the housing of the magnet apparatus is a trapezoidal housing with a diameter thereof at the skin facing side that is smaller than the diameter thereof at the side away from the skin facing side.

Figure 21:
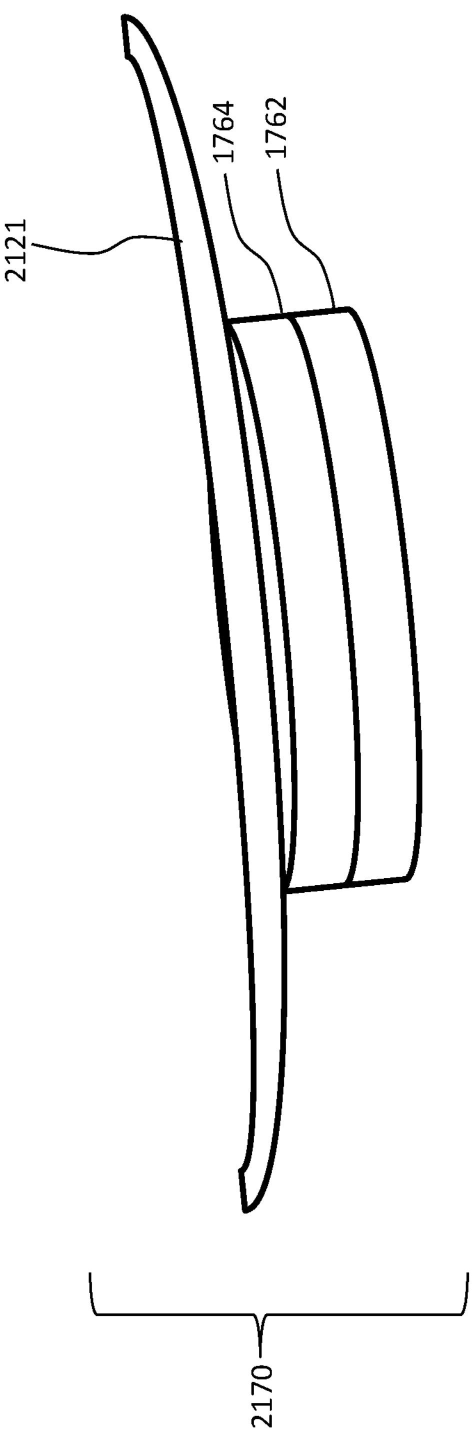
FIG. 21 presents another exemplary embodiment.

FIG. 21 presents another exemplary embodiment of an external device 2170, including components 1764 and 1762, and the magnet inside thereof, where rack apparatus 2121 is fixed to the top housing portion 1764. Rack 2121 can be a plastic flattened U shaped or C shaped component that can guide the bandages over the top of the external device/prevent the bandages from sliding the external device, and otherwise increase the surface area of contact of the bandages.

Consistent with the teachings above, in an exemplary embodiment, the assembly can be a puck, while in other embodiments, the assembly is a rectangular box (cube, or a square cross-section with a height that is not as high as the length and width of the square, or a rectangular cross-section with a height that is not as high as the length and/or width of the rectangle). An oval-shaped cross-section assembly can be utilized. Still, in an exemplary embodiment, a circular cross-section the body will be utilized.

Figure 19:
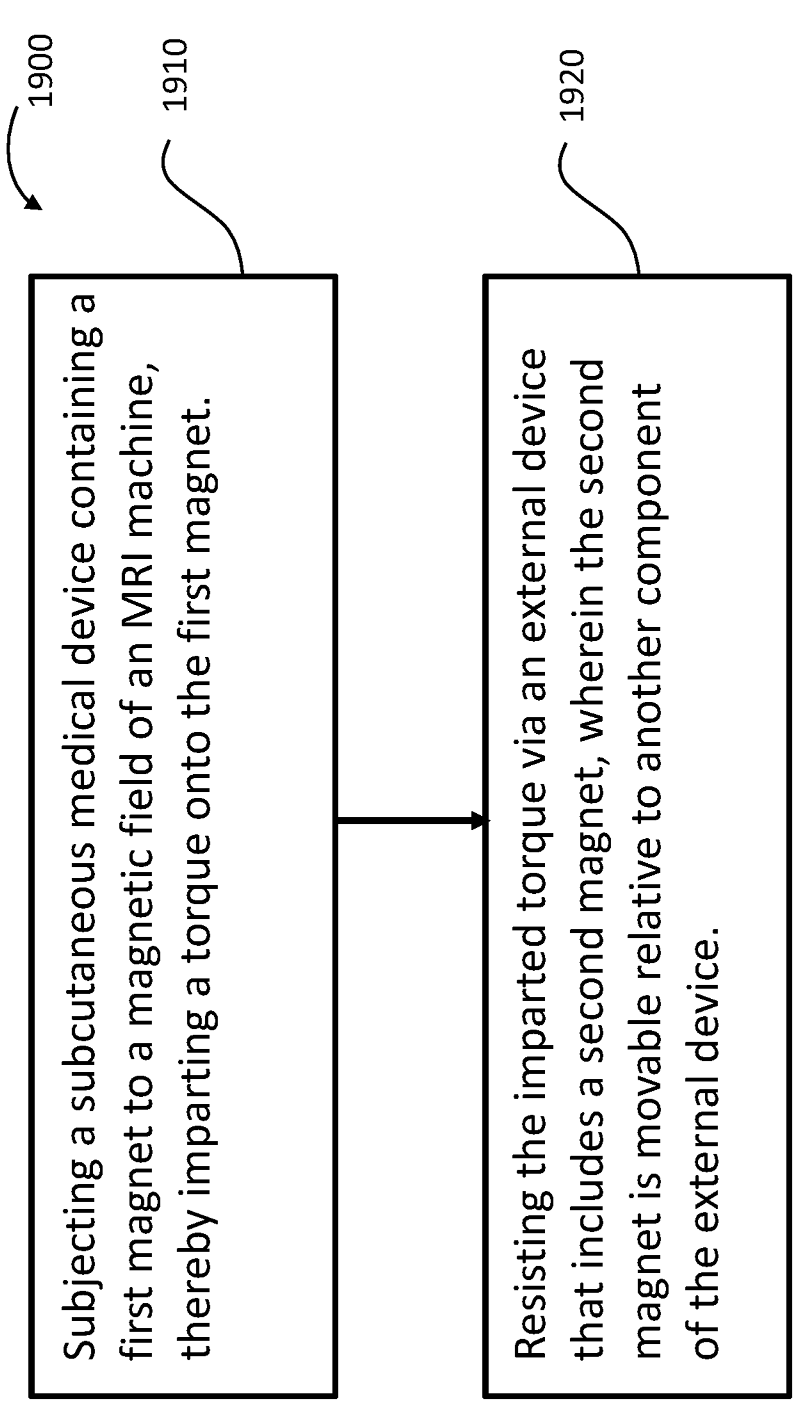
FIGS. 19 and 20 present exemplary flowcharts for exemplary embodiments.

FIG. 19 presents an exemplary flowchart for an exemplary method, method 1900. Method 1900 includes method action 1910, which includes subjecting a subcutaneous medical device containing a first magnet to a magnetic field of an MRI machine, thereby imparting a torque onto the first magnet. Method 1900 further includes method action 1920, which includes resisting the imparted torque via an external device that includes a second magnet, wherein the second magnet is movable relative to another component of the external device. Here, in this exemplary embodiment, the another component can be the splint and/or can be the housing containing the magnet, if a housing is present. This movement can be the axial and/or radial movement of the magnet and/or can be rotation of the magnet.

In an exemplary embodiment of method 1900, prior to the action of subjecting the subcutaneous medical device containing the first magnet to the magnetic field, the method further includes placing the external device against a head of a recipient over the first magnet so that the resulting magnetic force holds the external device above the first magnet. In an exemplary embodiment, the magnet in the external device is at least 1, 1.5, 2, 2.5, 3, 3.5, 4, 4.5, 5, 5.5, 6, 6.5, 7, 7.5, 8, 8.5, 9, 10, 11, 12, 13, 14, 15, 16, 17, 18, 19, or 20 times or more stronger than the magnet of the implanted device. In an exemplary embodiment, the magnetic attraction between the two magnets is such that a force of at least or no more than 0.1, 0.2, 0.3, 0.4, 0.5, 0.6, 0.7, 0.8, 0.9, 1, 1.25, 1.5, 1.75, 2, 2.25, 2.5, 2.75, 3, 3.5, 4, 4.5 or 5 Newtons applied at the base of the external device is required to move the external device more than 3 mm in the lateral direction where the external device is just the housing and/or splint without the belts or bandages or anything else other than the magnet attraction holding the external device to the recipient (no adhesives, etc.). In an exemplary embodiment, the magnetic attraction between the two magnets is such that a force of at least 0.1, 0.2, 0.3, 0.4, 0.5, 0.6, 0.7, 0.8, 0.9, 1, 1.25, 1.5, 1.75, 2, 2.25, 2.5, 2.75, 3, 3.5, 4, 4.5, 5, 5.5, 6, 6.5, 7, 8, or 9 Newtons must be applied to the external device to remove the external device from the recipient without the belts or bandages or anything else other than the magnet attraction holding the external device to the recipient.

In an exemplary embodiment, during method action 910, a magnetic attraction between the first magnet and the second magnet is reduced relative to that which was the case prior to the subjecting of the magnetic field. In an exemplary embodiment, the magnetic attractive force is reduced by less than or greater than 5, 10, 15, 20, 25, 30, 35, 40, 45, 50, 55, 60, 65, 70, 75, 80, 85, 90, 95, or 100%, or any value or range of values therebetween in 1 percent increments without demagnetization and/or in addition to any demagnetization of either of the magnets. In an exemplary embodiment, after the magnetic field is removed, the magnetic attractive force increases relative to that which was the case during the MRI filed application. In an exemplary embodiment, the magnetic attractive force increases to at least 70, 75, 80, 85, 90, 95, or 100% or any value or range of values therebetween in 1 percent increments relative to that which was the case prior to the application of the magnetic field.

In an exemplary embodiment, consistent with the teachings above, prior to the action of subjecting the subcutaneous medical device containing the first magnet to the magnetic field, there is an action of placing the external device against a head of a recipient over the first magnet so that the second magnet moves relative to the another component of the external device when the second magnet interacts with the magnetic field of the first magnet. In an exemplary embodiment, the movement of the magnet is the flipping as detailed above, while in other embodiments, the movement of the magnet is the rotation about one or more axes of the magnet. In an exemplary embodiment, the action of moving is a result of the magnetic field of the magnet of the external device aligning with the magnetic field of the implanted device.

As noted above, the teachings detailed herein can enhance the resistance to the torque applied to the magnetic field beyond that which would result from the skin alone and/or the implanted medical device alone. Still further, in at least some exemplary embodiments, as detailed above, the subcutaneous medical device is configured such that the magnet is removable from the subcutaneous medical device (e.g., through hole 180) by deforming silicone in an elastic manner, which silicone positions the magnet, without removing the subcutaneous medical device. In an exemplary embodiment, the medical device is configured such that the magnet can then be replaced. Such a feature can have utilitarian value with respect to a scenario where prior to subjecting the recipient to a magnetic field of an MRI machine, such as a magnetic field corresponding to, for example, 1T or more (e.g., 1.5T), the magnet is surgically removed. Then, after the recipient is subjected to an MRI magnetic field (and thus the remaining portions of the implant are also subjected to the MRI magnetic field), another surgery is executed to replace the magnet (which also includes placing a new magnet at the location of the old magnet) so that the full utilitarian value with respect to the implant can be achieved. Accordingly, the teachings detailed herein can be applicable to such a subcutaneous medical device, where instead of removing the magnet prior to subjecting the implantable component to the MRI magnetic field, the teachings detailed herein are applied so as to render such surgery unnecessary. In view of the above, in at least some exemplary embodiments, the action of subjecting the subcutaneous medical device containing the magnet to the magnetic field entails subjecting the magnet to at least a 1.5T magnetic field without magnet dislocation. That is, the magnet may move a bit in some instances, but the magnet will not be dislocated from the housing of the implant containing the magnet. In an exemplary embodiment, the method is executed with respect to the aforementioned magnetic field, and the housing of the implant only elastically deforms. That is, in an exemplary embodiment, there is no plastic deformation of the housing. In an exemplary embodiment, any plastic deformation of the housing that occurs is de minimis from a standpoint of continued use of the implantable component. In an exemplary embodiment, the aforementioned scenarios result with respect to a magnetic field that corresponds to or more than 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 or 3.5 or 4 or 4.5 or 5 or 5.5 or 6 T, or any values or range of values therebetween in 0.05 T increments.

In an exemplary embodiment of method 1900, the subcutaneous medical device is configured such that the first magnet is removable from the subcutaneous medical device by deforming silicone that positions the first magnet without removing the subcutaneous medical device from the recipient. Further, in an exemplary embodiment, the action of subjecting the subcutaneous medical device containing the first magnet to the magnetic field includes subjecting the magnet to at least a 1, 1.5, 2, 2.5, 3, 3.5, 4, 4.5, 5, 5.5, or 6T magnetic field without first magnet dislocation.

Figure 20:
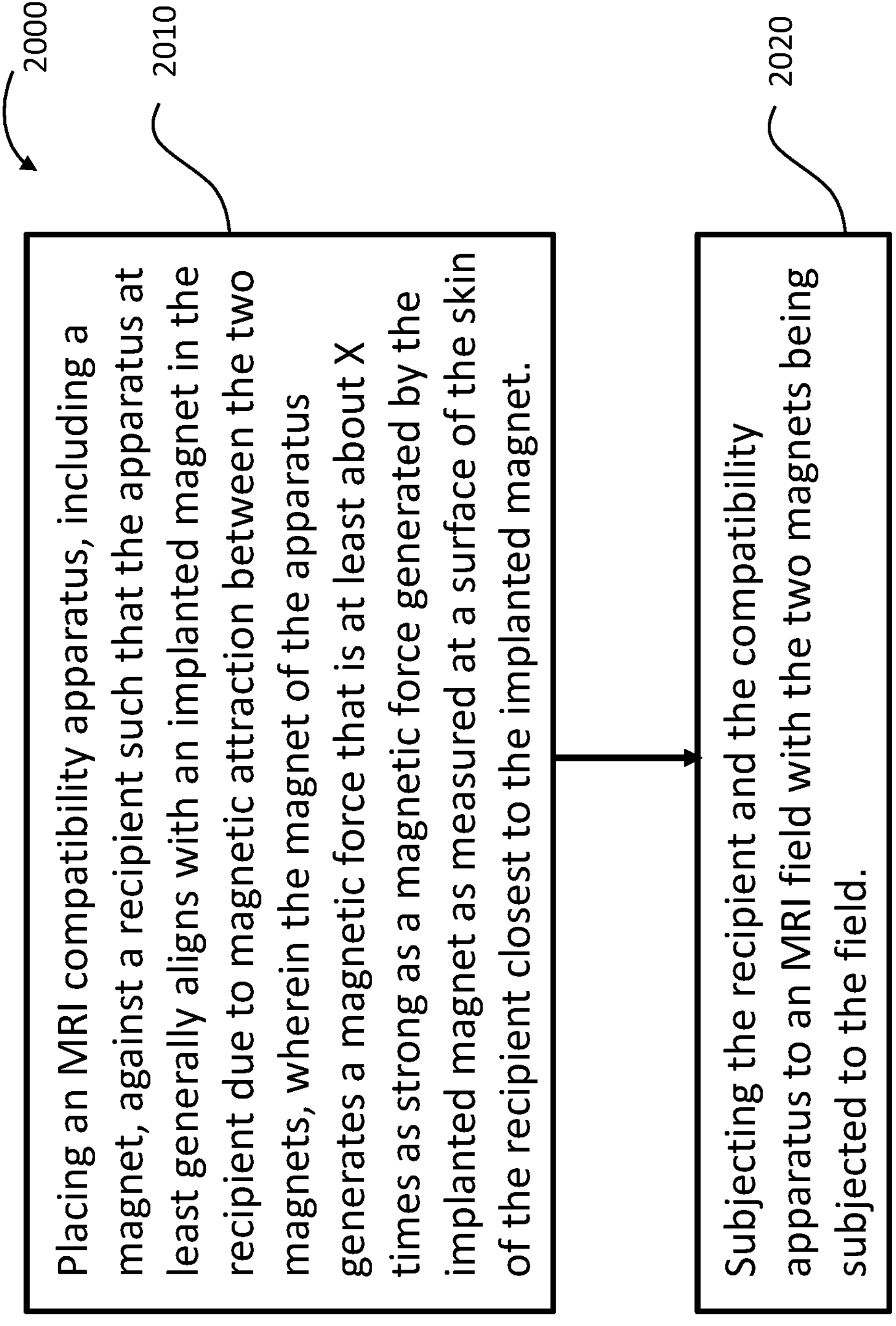

FIG. 20 presents another exemplary flowchart for an exemplary method, method 2000, which includes method action 2010, which includes placing an MRI compatibility apparatus, including a magnet, against a recipient such that the apparatus at least generally aligns with an implanted magnet in the recipient due to magnetic attraction between the two magnets, wherein the magnet of the apparatus generates a magnetic force that is at least about X or no more than about X times as strong as a magnetic force generated by the implanted magnet as measured at a surface of the skin of the recipient closest to the implanted magnet. In an exemplary embodiment, X is 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 10, 11, 12, 13, 14, 15, 16, 17, 18, 19, or 20. Method 2000 further includes method 2020, which includes subjecting the recipient and the compatibility apparatus to an MRI field with the two magnets being subjected to the field.

In an exemplary embodiment, as noted above, magnets detailed herein that are part of the MRI compatibility device are configured to be effectively demagnetized when subjected to a MRI magnetic field when the magnet is used on the head of a recipient (other embodiments, the magnet is configured so that the magnet will be effectively not demagnetized—in some embodiments, the amount of demagnetization is less than or greater than 0.1, 0.2, 0.3, 0.4, 0.5, 0.6. 0.7. 0.8. 0.9, 1, 1.25, 1.5, 1.75. 2, 2.5, 3, 3.5, 4, 4.5, 5, 6. 7, 8. 9, 10, 11, 12, 13, 14, 15, 16, 17, 18, 19, 20, 21, 22, 23, 24, 25, 30, 35 or 40 percent relative to its original field strength when subjected to 5, 10, 15, 20, 25, 30, 35, 40, 45, 50, 55, 60, 70, 80, 90, 100, 110, 120 or more minutes of an MRI magnetic field of at least 0.25, 0.5, 0.75, 1, 1.5, 2, 2.5, 3, 3.5, 4, 4.5, 5, 5.5T and/or 6T). Concomitant with this embodiment, method 2000 can include the action of subjecting the magnet of the apparatus to the MRI field such that the magnet is effectively demagnetized. In this regard, there is utilitarian value in using the magnet to align the compatibility device with the implanted magnet via interactions with the respective magnetic field. This is done before the recipient is exposed to the MRI field. The bandages/belts, or whatever position maintenance scheme that is utilized retains the compatibility device in position, and thus should generally maintain the alignment of the device with the implanted magnet. Then, upon subjecting the recipient to the MRI magnetic field, the external magnet of the compatibility device effectively becomes demagnetized, for example, within the aforementioned temporal periods. In some embodiments, the artefact that results from the external magnet (or whatever it is to be referred after demagnetization) is reduced by 5, 6, 7, 8, 9, 10, 15, 20, 25, 30, 35, 40, 45, 50, 55, 60, 65, 70, 75, 80, 85, 90 or 95% or more or 100% or any value or range of value therebetween in 0.1% relative to that which would have been the case in the absence of the reduction of magnetism, all other things being equal. In an exemplary embodiment, the reduction of torque applied to the external magnet (herein, an effectively demagnetized magnet demagnetized by the MRI field is still referred to as "the magnet" for the methods) directly by the MRI magnetic field is reduced by 5, 6, 7, 8, 9, 10, 15, 20, 25, 30, 35, 40, 45, 50, 55, 60, 65, 70, 75, 80, 85, 90 or 95% or more or 100% relative to that which would have been the case in the absence of the reduction of magnetism, all other things being equal.

In an exemplary embodiment, a torque applied to the MRI compatibility device as a result of the direct interaction of the MRI magnetic field with the external magnet (as opposed to the implanted magnet) is reduced by 5, 6, 7, 8, 9, 10, 15, 20, 25, 30, 35, 40, 45, 50, 55, 60, 65, 70, 75, 80, 85, 90 or 95% or more or 100% relative to that which would have been the case in the absence of the magnets ability to move, all other things being equal.

In an exemplary embodiment of method 2000, that further includes the action of applying a holding apparatus to the compatibility apparatus that applies at least one of a downward force onto the compatibility apparatus or a lateral positioning force onto the compatibility apparatus. As seen above, in an exemplary embodiment, this holding apparatus can be a belt and/or can be a bandage such as a fabric bandage. Indeed, in an exemplary embodiment, method 2000 further includes the action of wrapping a fabric around a head of the recipient with the MRI compatibility apparatus interposed between the fabric and the head of the recipient, wherein the magnetic attraction between the two magnets maintains the general position of the compatibility apparatus over the implanted magnet during the action of wrapping. In this regard, the action of bandaging can be a forceful undertaking. That is, for example, the bandage should be applied such that the resulting tensile force on the bandage results in a sufficient compression force onto the MRI compatibility apparatus in general, and the splint and/or the magnet apparatus in particular, so that the magnet that is implanted does not move beyond that which is desirable. Accordingly, the action of wrapping the fabric around a head of the recipient could be forceful, and thus there can be utilitarian value with respect to the magnetic attraction between the magnet apparatus and the implanted magnet being such that with at least a modicum of care by the healthcare professional it is wrapping the bandage about the head of the recipient, the general position of the compatibility apparatus is maintained during the action of wrapping.

Additionally, in the embodiments where the magnet of the splint can rotate itself to align with strong magnetic field of the MRI machine, the force and/or the torque applied to a recipient's head may be reduced relative to that which would otherwise be the case in the absence of the ability to rotate, all other things being equal (e.g., initial holding force between the implant and the splint). In an exemplary embodiment, the amount of force and/or the torque applied to the recipient's head is reduced by at least 5, 6, 7, 8, 9, 10, 15, 20, 25, 30, 35, 40, 45, 50, 55, 60, 65, 70, 75, 80, 85, 90 or 95% or more or 100% or any value or range of value therebetween in 0.1% increments, relative to a non-moving/non-rotating magnet, all other things being equal. Corollary to this is that the rotating magnet can be more easily/better attracted to the implanted magnet relative to a fixed magnet, all other things being equal, such that, for a given magnetic volume/field generated by the external magnet/average artefact size resulting from the magnet, the attractive force can be at least 5, 10, 15, 20, 25, 30, 35, 40, 45, 50, 60, 70, 80, 90, 100, 125, 150, 175, 200, 250 or 300 percent or more or any value or range of values therebetween in 0.1% increments relative that which would be the case for a fixed magnet, all other things being equal.

Moreover, in some embodiments, the image artefact resulting in the obtained MRI images can be reduced relative to a fixed magnet, all other things being equal (holding force, initial magnetic field strength, etc.), by, for example, 5, 6, 7, 8, 9, 10, 15, 20, 25, 30, 35, 40, 45, 50, 55, 60, 65, 70, 75 or 80% or more or any value or range of values therebetween in 0.1% increments by size (area, maximum distance/diameter, etc.).

Also, in an exemplary embodiment, there is an exemplary method of executing method 1900 H times. In this exemplary embodiment, method action 1910 is executed H times for different and/or the same recipients using different and/or the same hardware. Method action 1920 is also executed H times for the respective recipients the subject of method action 1910 using different and/or the same hardware. In an exemplary embodiment, this can be achieved by utilizing the pertinent embodiments detailed herein and/or variations thereof. In an exemplary embodiment, H equals 5 times, 6 times, 7 times, 8 times, 9 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 35 times, 40 times, 45 times, 50 times, or more, all within 6, 7, 8, 9, 10, 11, 12, 13, 14, 15, 16, 17, 18, 19, 20, 21, 22, 23, 24, 25, 26, 27, 28, 29 or 30 months.

Also, in an exemplary embodiment, there is an exemplary method of executing method 2000 H times. In this exemplary embodiment, method action 2010 is executed H times for different and/or the same recipients using different and/or the same hardware. Method action 2020 is also executed H times for the respective recipients the subject of method action 2010 using different and/or the same hardware. In an exemplary embodiment, this can be achieved by utilizing the pertinent embodiments detailed herein and/or variations thereof. In an exemplary embodiment, the H times are executed within 3, 4, 5, 6, 7, 8, 9, 10, 11, 12, 13, 14, 15, 16, 17, 18, 19, 20, 21, 22, 23, 24, 25, 26, 27, 28, 29, 30, 36, 42, or 48 months, or any value or range of values therebetween in 1 month increments.

In view of the above, there is an exemplary method that includes the action of subjecting subcutaneous medical devices (whether the same or different) containing respective first magnets to respective magnetic fields of respective MRI machines H times, thereby imparting respective torques onto the respective first magnets magnet. The method further includes respectively resisting the respective imparted torques via respective use of an external device that includes a second magnet, the external device being a same device or different devices for the respective resisting actions (e.g., the same one can be used for all or different ones can be used for some or all (the device could be disposable), wherein the second magnet is movable relative to another component of the external device. Further, prior to the respective actions of subjecting the subcutaneous medical device containing the first magnet to the magnetic field, respectively placing the external device against respective heads of respective recipients (which can be the same recipient or different recipients—the "respective" refers to the individual actions) over the first magnet so that the resulting magnetic force aligns the external device above the first magnet such that a geometric center of the external device is within 0.5, 0.75, 1, 1.25, 1.5, 1.75, 2, 2.5, 3, 3.5, 4, 4.5, 5, 5.5, 6, 6.5, 7, 7.5, or 8 mm or any value or range of values therebetween in 0.1 mm increments of an axis extending through a geometric center of the first magnet and normal to a skin surface immediately above the first magnet. In some embodiments, all of the above are executed within any of the aforementioned time periods.

Also, in an exemplary embodiment, there is a method that includes repeating the actions of subjecting the subcutaneous medical devices to the respective magnetic fields at least any of the aforementioned number of times within any of the aforementioned temporal periods and respectively resisting the respective imparted torques, wherein prior to the actions of subjecting the subcutaneous medical device containing the first magnet to the magnetic field, the external device is placed against a head of a recipient over the first magnet, whether the same external device or different external devices, so that the resulting magnetic force holds the external device above the first magnet and the resulting magnetic force aligns the external device with the first magnet. Further, a magnetic orientation of the second magnet and a magnetic strength thereof remains within 90% of respective values that were present prior to the first time that the second magnet was exposed to the magnetic field for the respective repetitions of the actions.

In an exemplary embodiment, as measured by area and/or by maximum distance, the results of any of the methods detailed herein are such that the resulting artifact in the resulting MRI image from the magnet of the external device is less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35% of that which would be the case in the absence of the external device without the external magnet, all other things being equal/in addition to the artifact created by the implanted magnet, all other things being equal.

Briefly, in at least some embodiments, because the magnet can rotate itself/be rotated by the magnetic field to align with strong magnetic field of the MRI machine, the demagnetization of the magnet of the splint can be avoided/mitigated, in at least some embodiments. In an exemplary embodiment, there is a method that utilizes the devices herein 5, 10, 15, 20, 25, 30, 35, 40, 45, 50, 60, 70, 80, 90 or 100 times or more in an MRI machine that is or is greater than a 1.5, 2, 2.5, 3, 3.5, 4 T machine, where the amount of demagnetization is less than 1, 2, 3, 4, 5, 6, 7, 8, 9, 10, 15, 20, 25, 30, 35 or 40% after the aforementioned cycles (with respect to a strength of the field).

It is further noted that in at least some exemplary embodiments, the surface of the magnet apparatus is augmented so as to make handling thereof easier relative to that which be the case with a perfectly smooth surface. By way of example only and not by way of limitation, in an exemplary embodiment, ribs, bumps, and/or a roughened surface is provided to various surfaces of the magnet apparatus (i.e., the surface facing away from the skin of the recipient). In an exemplary embodiment, these are molded into the housing of the magnet apparatus. In some embodiments, there are surface features that "grip" the bandage or otherwise hold the bandage.

It is noted that any method detailed herein also corresponds to a disclosure of a device and/or system configured to execute one or more or all of the method actions detailed herein. It is further noted that any disclosure of a device and/or system detailed herein corresponds to a method of making and/or using that the device and/or system, including a method of using that device according to the functionality detailed herein.

It is further noted that any disclosure of a device and/or system detailed herein also corresponds to a disclosure of otherwise providing that device and/or system.

It is noted that in at least some exemplary embodiments, any feature disclosed herein can be utilized in combination with any other feature disclosed herein unless otherwise specified. Accordingly, exemplary embodiments include a medical device including one or more or all of the teachings detailed herein, in any combination.

Embodiments include any feature disclosed herein combined with any other feature disclosed herein unless otherwise noted. Embodiments also include any feature disclosed herein excluded from combination with any other feature disclosed herein unless otherwise noted.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. An MRI compatibility assembly, comprising:

a first component configured to interface with skin of a recipient at a location overlying an implanted magnet of an implantable component; and a magnet including, for a given orientation relative to the first component, a first surface area facing the first component and a second surface area opposite the first surface area; and a casing assembly, wherein the magnet is supported by the first component and the casing assembly, the casing assembly includes a plurality of pieces including a first piece and a second piece, the first piece extending between the first surface area of the magnet and the first component, the second piece extending over the second surface area of the magnet, the casing assembly establishing a cavity when the plurality of pieces are assembled, the magnet is housed in the cavity and movable relative to the first component and the casing assembly, and the MRI compatibility assembly is configured to be exposed to at least a 1T magnetic field of an MRI machine.

2. The MRI compatibility assembly of claim 1, wherein:

the magnet supported by the first component is a disk magnet, and the disk magnet is rotatable about an axis thereof.

3. The MRI compatibility assembly of claim 1, wherein:

the MRI compatibility assembly is configured to be placed against the recipient such that the MRI compatibility assembly at least generally aligns with the implanted magnet.

4. The MRI compatibility assembly of claim 1, wherein:

the MRI compatibility assembly is configured to be exposed to at least a 3T magnetic field of an MRI machine for at least 30 minutes.

5. The MRI compatibility assembly of claim 1, wherein: the MRI compatibility assembly is configured such that the magnet supported by the first component automatically aligns the first component over the implanted magnet.

6. The MRI compatibility assembly of claim 1, wherein: the MRI compatibility assembly is configured so that the magnet always experiences little to no torque thereon as a result of the at least 1T magnetic field acting directly thereon.

7. The MRI compatibility assembly of claim 1, wherein: the MRI compatibility assembly is configured to be exposed to at least a 3T magnetic field of an MRI machine.

8. The MRI compatibility assembly of claim 1, wherein: the MRI compatibility assembly is configured to be exposed to at least a 3 T magnetic field of an MRI machine for at least 15 minutes.

9. The MRI compatibility assembly of claim 1, wherein: a height of the MRI compatibility assembly is at least about half of a maximum diameter thereof.

10. The MRI compatibility assembly of claim 1, wherein: the MRI compatibility assembly is configured to resist a torque imparted onto the implanted magnet of the implantable component.

11. The MRI compatibility assembly of claim 1, wherein: the magnet supported by the first component is magnetically coupled to the implanted magnet; and the magnet supported by the first component generates a magnetic force that is at least about 2 times as strong as a magnetic force generated by the implanted magnet of the implantable component.

12. The MRI compatibility assembly of claim 1, wherein: a height of the MRI compatibility assembly is more than a maximum diameter of the magnet supported by the first component.

13. The MRI compatibility assembly of claim 1, wherein: the MRI compatibility apparatus interfaces with no more than about 4,000 $mm^2$ of recipient body surface when the magnet supported by the first component interacts with the implanted magnet of the implantable component.

14. The MRI compatibility assembly of claim 1, wherein: the first component indirectly supports the magnet.

15. The MRI compatibility assembly of claim 1, wherein: the magnet supported by the first component is a magnet that produces a magnetic field of at least about a half of a tesla.

16. The MRI compatibility assembly of claim 1, wherein: the magnet supported by the first component is a spherical magnet, and the spherical magnet rotates when it interacts with the magnetic field of the MRI machine.

17. The MRI compatibility assembly of claim 1, wherein: the MRI compatibility assembly has a skin interfacing side surface that is between 30 mm and 60 mm at its maximum diameter.

18. The MRI compatibility assembly of claim 1, wherein: a maximum diameter of the MRI compatibility assembly at a location away from a skin interfacing portion is larger than a maximum diameter of the MRI compatibility assembly at a location proximate the skin interfacing portion.

19. The MRI compatibility assembly of claim 1, wherein: the MRI compatibility assembly is a puck.

20. The MRI compatibility assembly of claim 1, wherein: the MRI compatibility assembly is configured to be exposed to at least a 1T magnetic field of an MRI machine for at least 15 minutes.

21. The MRI compatibility assembly of claim 20, wherein:
the magnet supported by the first component is a spherical magnet, and the spherical magnet rotates when it interacts with the magnetic field of the MRI machine.

22. The MRI compatibility assembly of claim 20, wherein:
the magnet supported by the first component is a magnet that produces a magnetic field of at least about a half of a tesla.

23. The MRI compatibility assembly of claim 20, wherein:
the MRI compatibility assembly has a skin interfacing side surface that is between 30 mm and 60 mm at its maximum diameter.

24. The MRI compatibility assembly of claim 20, wherein:
a maximum diameter of the MRI compatibility assembly at a location away from a skin interfacing portion is larger than a maximum diameter of the MRI compatibility assembly at a location proximate the skin interfacing portion.

25. The MRI compatibility assembly of claim 20, wherein:
the MRI compatibility assembly is configured to be exposed to at least a 1T magnetic field of an MRI machine for at least 60 minutes.

26. The MRI compatibility assembly of claim 20, wherein:
the MRI compatibility assembly is a puck.

27. A method, comprising:
placing an MRI compatibility apparatus including a second magnet and a first component configured to interface with a skin of a recipient at a location overlaying a first magnet, implanted beneath the skin of the recipient, of an implanted medical device implanted in the recipient, against the recipient such that the MRI compatibility apparatus at least generally aligns with the first magnet of the implanted medical device implanted in the recipient via magnetic interaction with the first magnet;
subjecting the medical device containing the first magnet to a magnetic field of an MRI machine, thereby imparting a torque onto the first magnet; and
resisting the imparted torque via the MRI compatibility apparatus that includes the second magnet, wherein
the second magnet includes, for a given orientation relative to the first component, a first surface area facing the first component and a second surface area opposite the first surface area,
the MRI compatibility apparatus further includes a casing assembly,
the second magnet is supported by the first component and the casing assembly,
the casing assembly includes a plurality of pieces including a first piece and a second piece, the first piece extending between the first surface area of the second magnet and the first component, the second piece extending over the second surface area of the second magnet, the casing assembly establishing a cavity when the plurality of pieces are assembled, and
the second magnet is housed in the cavity and movable relative to the first component and the casing assembly.

28. The method of claim 1, wherein the action of placing the MRI compatibility apparatus against the recipient includes placing the MRI compatibility apparatus against a head of the recipient over the first magnet so that the second magnet moves relative to the first component of the MRI compatibility apparatus when the second magnet interacts with the magnetic field of the first magnet.

29. A method, comprising:

placing an MRI compatibility apparatus, including a magnet, against a recipient such that the MRI compatibility apparatus at least generally aligns with an implanted magnet in the recipient due to magnetic attraction between the magnet of the MRI compatibility apparatus and the implanted magnet, wherein the magnet of the MRI compatibility apparatus generates a magnetic force that is at least about 2 times as strong as a magnetic force generated by the implanted magnet as measured at a surface of the skin of the recipient closest to the implanted magnet; and subjecting the recipient and the MRI compatibility apparatus to an MRI field with the two magnets being subjected to the field, wherein the MRI compatibility apparatus includes:

a first component configured to interface with skin of a recipient at a location overlying an implanted magnet of an implantable component; and a casing assembly, wherein the magnet of the MRI compatibility apparatus includes, for a given orientation relative to the first component, a first surface area facing the first component and a second surface area opposite the first surface area, the magnet of the MRI compatibility apparatus is supported by the first component and the casing assembly, the casing assembly includes a plurality of pieces including a first piece and a second piece, the first piece extending between the first surface area of the magnet MRI compatibility apparatus and the first component, the second piece extending over the second surface area of the magnet, the casing assembly establishing a cavity when the plurality of pieces are assembled, and the magnet MRI compatibility apparatus is housed in the cavity and movable relative to the first component and the casing assembly.

30. The method of claim 29, further comprising:

wrapping a fabric around a head of the recipient with the MRI compatibility apparatus interposed between the fabric and the head of the recipient, wherein the magnetic attraction between the two magnets maintains the general position of the MRI compatibility apparatus over the implanted magnet during the action of wrapping.

* * * * *